US012594305B2

(12) United States Patent
Moreno

(10) Patent No.: US 12,594,305 B2
(45) Date of Patent: Apr. 7, 2026

(54) BONE MARROW MICROGLIA PROGENITOR CELLS AND USES THEREOF

(71) Applicant: Strominnate Therapeutics AB, Lund (SE)

(72) Inventor: Tania Ramos Moreno, Lund (SE)

(73) Assignee: Strominnate Therapeutics AB, Lund (SE)

( * ) Notice: Subject to any disclaimer, the term of this patent is extended or adjusted under 35 U.S.C. 154(b) by 1122 days.

(21) Appl. No.: 17/615,679

(22) PCT Filed: Jun. 4, 2020

(86) PCT No.: PCT/EP2020/065494
§ 371 (c)(1),
(2) Date: Dec. 1, 2021

(87) PCT Pub. No.: WO2020/245276
PCT Pub. Date: Dec. 10, 2020

(65) Prior Publication Data
US 2022/0241344 A1      Aug. 4, 2022

(30) Foreign Application Priority Data

Jun. 4, 2019   (EP) .................................... 19178278

(51) Int. Cl.
| | |
|---|---|
| *A61K 35/30* | (2015.01) |
| *C12N 5/073* | (2010.01) |
| *C12N 5/074* | (2010.01) |
| *C12N 5/079* | (2010.01) |
| *C12N 5/0797* | (2010.01) |

(52) U.S. Cl.
CPC ............ *A61K 35/30* (2013.01); *C12N 5/0605* (2013.01); *C12N 5/0607* (2013.01); *C12N 5/0622* (2013.01); *C12N 5/0623* (2013.01); *C12N 2501/052* (2013.01); *C12N 2501/13* (2013.01); *C12N 2501/15* (2013.01); *C12N 2501/22* (2013.01); *C12N 2501/2334* (2013.01); *C12N 2502/1358* (2013.01)

(58) Field of Classification Search
None
See application file for complete search history.

(56) References Cited

U.S. PATENT DOCUMENTS 10,081,792 B2    9/2018  Thomson et al.

OTHER PUBLICATIONS

Schehr et al., "High Specificity in Circulating Tumor Cell Identification Is Required for Accurate Evaluation of Programmed Death-Ligand 1", Plos One, 2016, 11(7), pp. 1-15. (Year: 2016).*

Cruz et al., "CD11b+ and Sca-1+ Cells Exert the Main Beneficial Effects of Systemically Administered Bone Marrow-Derived Mononuclear Cells in a Murine Model of Mixed Th2/Th17 Allergic Airway Inflammation", Stem cells Translation Medicine, 2016, vol. 5, pp. 488-499. (Year: 2016).*
Bohlen et al., "Diverse requirements for microglial survival, specification, and function revealed by defined-medium cultures", Neuron 94, 759-773.e758, 2017.
Butovsky et al., "Identification of a Unique TGF-b Dependent Molecular and Functional Signature in Microglia", Nature Neuroscience 17, 131-143, 2014.
Ginhoux et al., "Fate Mapping Analysis Reveals That Adult Microglia Derive from Primitive Macrophages", Science 330, 841-845, 2010.
Hickman et al., "The Microglial Sensome Revealed by Direct RNA Sequencing", Nature Neuroscience 16, 1896-1905, 2010.
Hinze et al., "Differentiation of mouse bone marrow derived stem cells toward microglia-like cells", BMC Cell Biology 12(1), 35, 2011.
Hinze et al., "Microglia differentiation using a culture system for the expansion of mice non-adherent bone marrow stem cells", Journal of Inflammation 9 (1), 12, 2012.
Kierdorf et al., "Microglia emerge from erythromyeloid precursors via Pu.1- and irf8-dependent pathways", Nature Neuroscience 16, 273, 2013.
Muffat et al., "Efficient derivation of microglia-like cells from human pluripotent stem cells", Nat med 22, 1358-1367, 2016.
Nikodemova et al., "Efficient isolation of live microglia with preserved phenotypes from adult mouse brain", Journal of Neuroinflammation, 9(1), 147, 2012.
Pandya et al., "Differentiation of human and murine induced pluripotent stem cells to microglia-like cells", Nature Neuroscience 20, 753-759, 2017.
Rahmat et al., "Reciprocal interactions of mouse bone marrowderived mesenchymal stem cells and BV2 microglia after lipopolysaccharide stimulation", Stem Cell Research & Therapy 4(1), 12, 2013.
Schulz et al., "A Lineage of Myeloid Cells Independent of Myb and Hematopoietic Stem Cells", Science 336, 86-90, 2012.
Yang et al., "Changes in phenotype and differentiation potential of human mesenchymal stem cells aging in vitro", Stem Cell Research and Therapy 9, 131, 2018.
Zanier et al., "Bone Marrow Mesenchymal Stromal Cells Drive Protective M2 Microglia Polarization After Brain Trauma", Neurotherapeutics 11, 679-695, 2014.
Zhang et al., "An RNA-Sequencing Transcriptome and Splicing Database of Glia, Neurons, and Vascular Cells of the Cerebral Cortex", The Journal of Neuroscience 34, 11929-11947, 2014.
Bruzelius, A. et al., The human bone marrow harbors a CD45–CD11B+ cell progenitor permitting rapid microglia-like cell derivative approaches, Stem Cells Translational Medicine, 10(4): 582-597, Apr. 2021.

(Continued)

*Primary Examiner* — Laura Schuberg
(74) *Attorney, Agent, or Firm* — Weston R. Gould; Dinsmore & Shohl LLP

(57) ABSTRACT

The present disclosure concerns a microglia progenitor cell derived from bone marrow and/or placental stromal cells and/or umbilical cord stromal cell and methods for their isolation; as well as use of said cells for therapy of disorders of the CNS.

6 Claims, 15 Drawing Sheets

(56) References Cited

OTHER PUBLICATIONS

Harry, G., Microglia During Development and Aging, Pharmacol
Ther., 139(3): 313-326, Sep. 2013.

* cited by examiner

Figure 2, cont.
B.
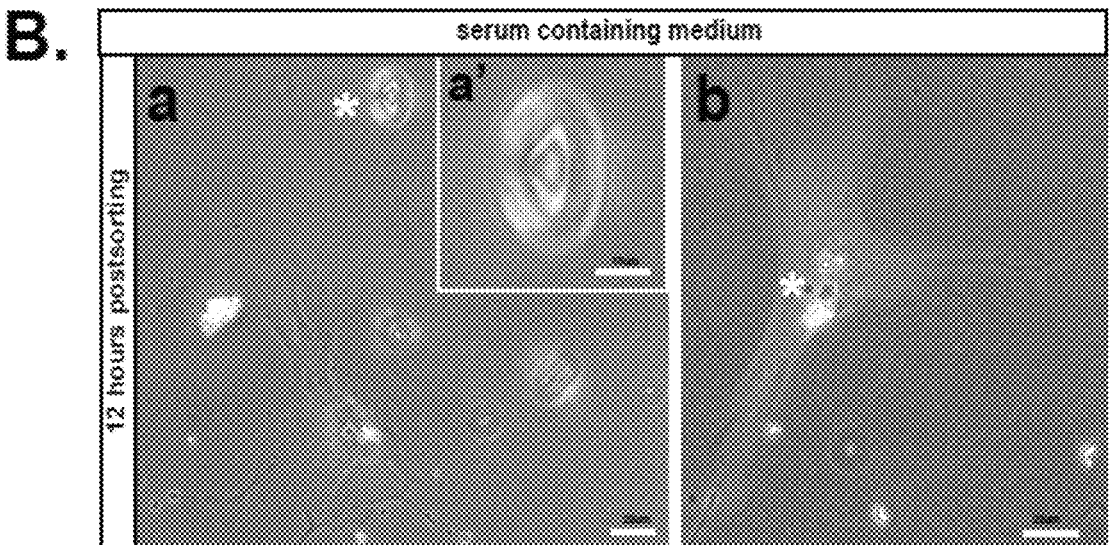
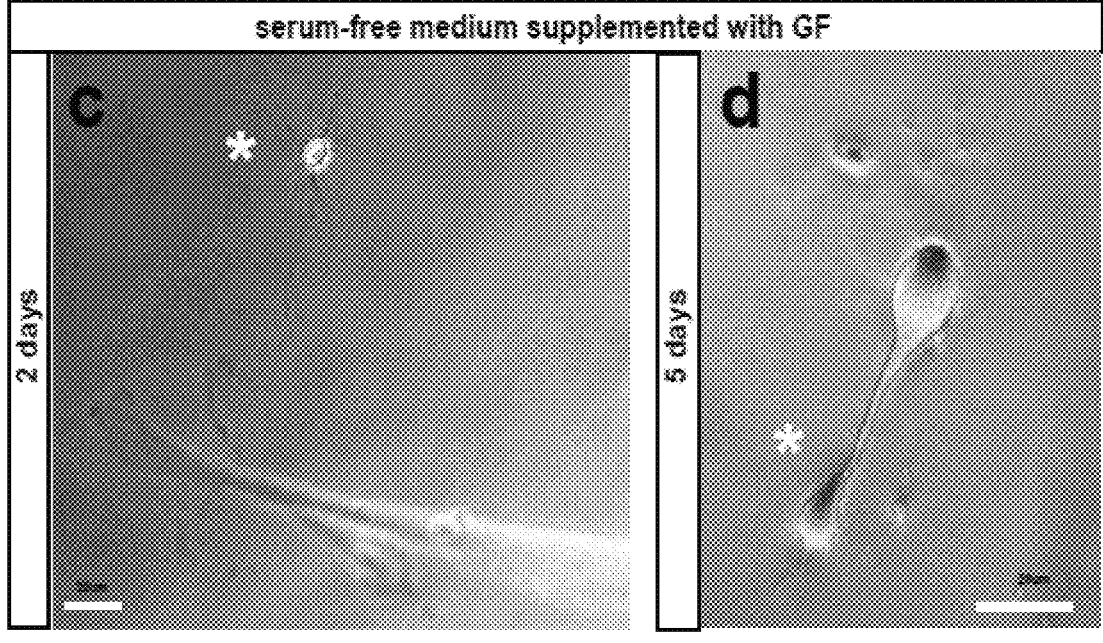

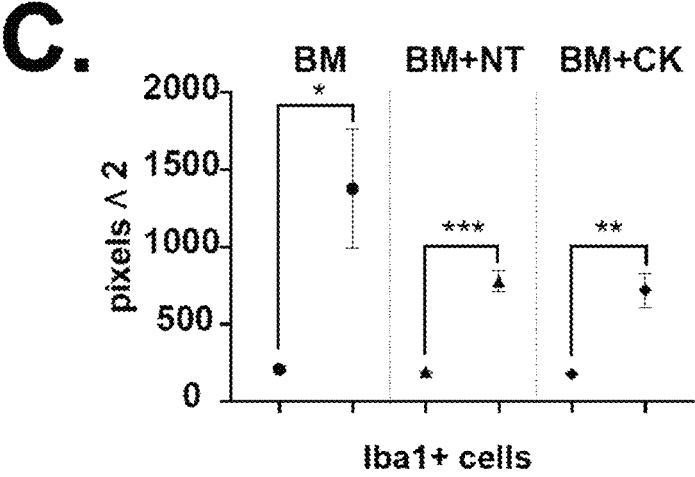
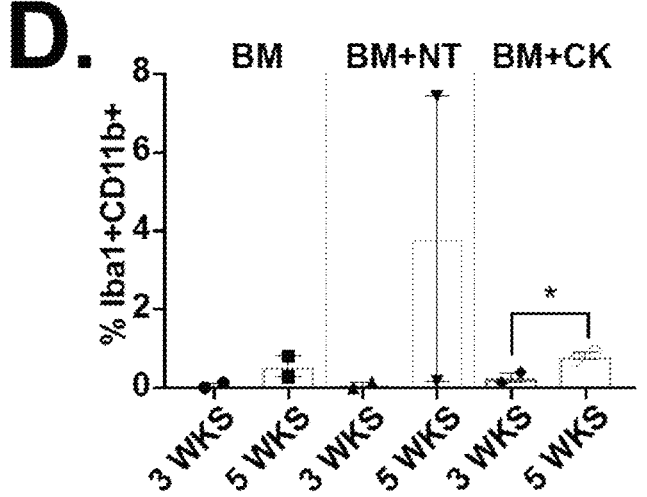
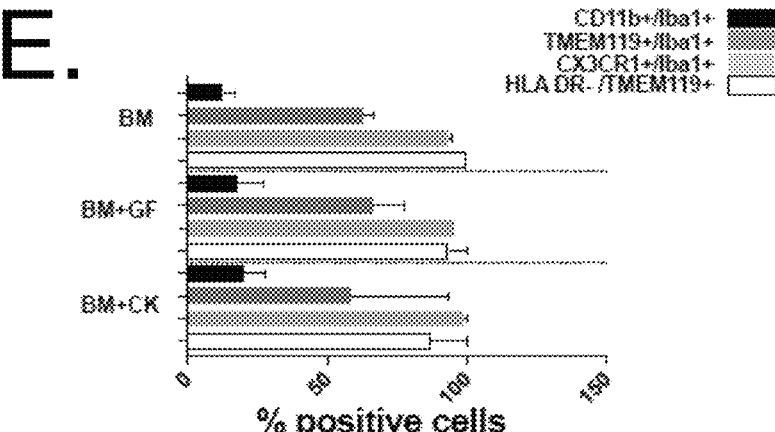
FIG. 2, cont.

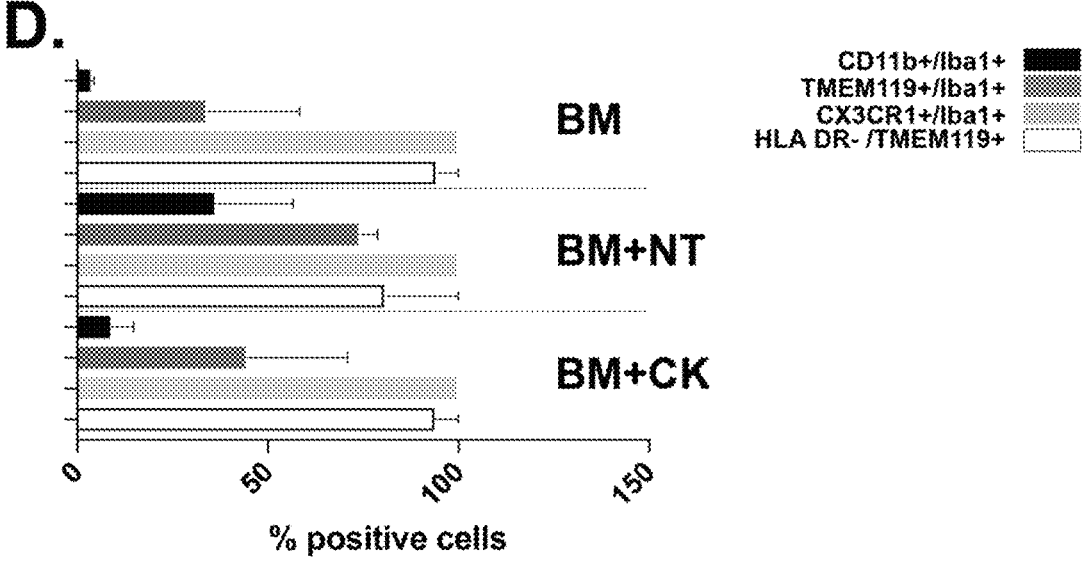
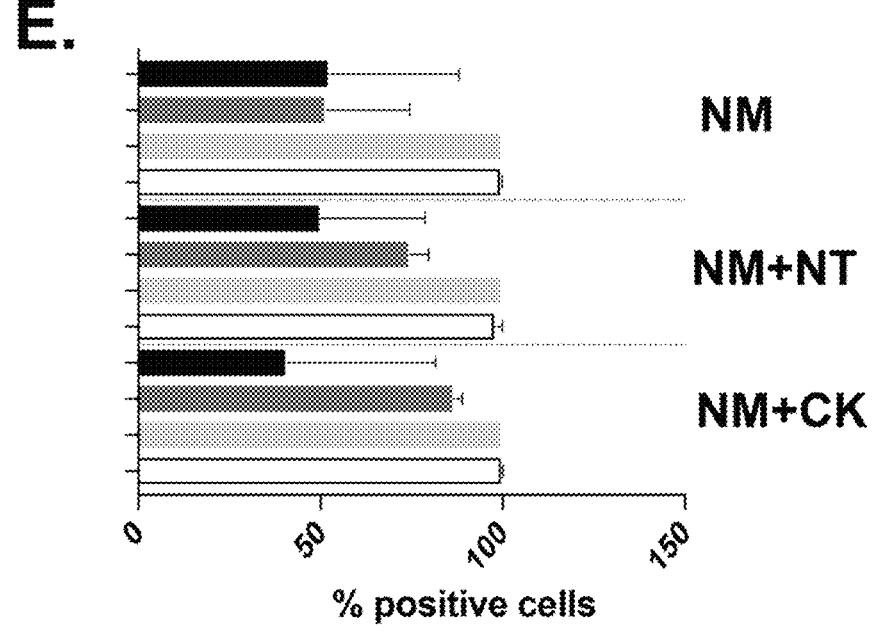
FIG. 4, cont.

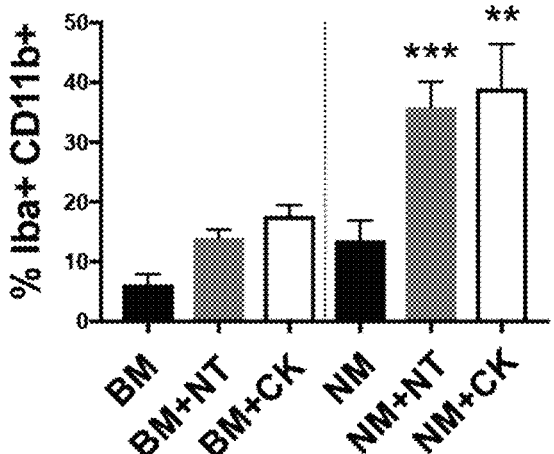
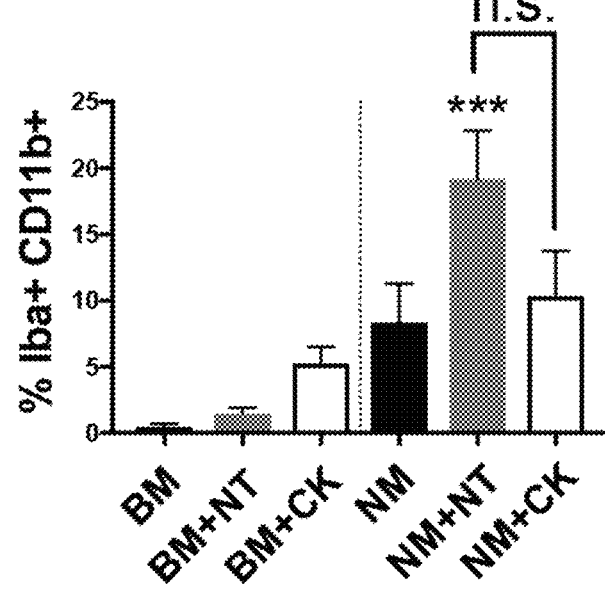
FIG. 4, cont.

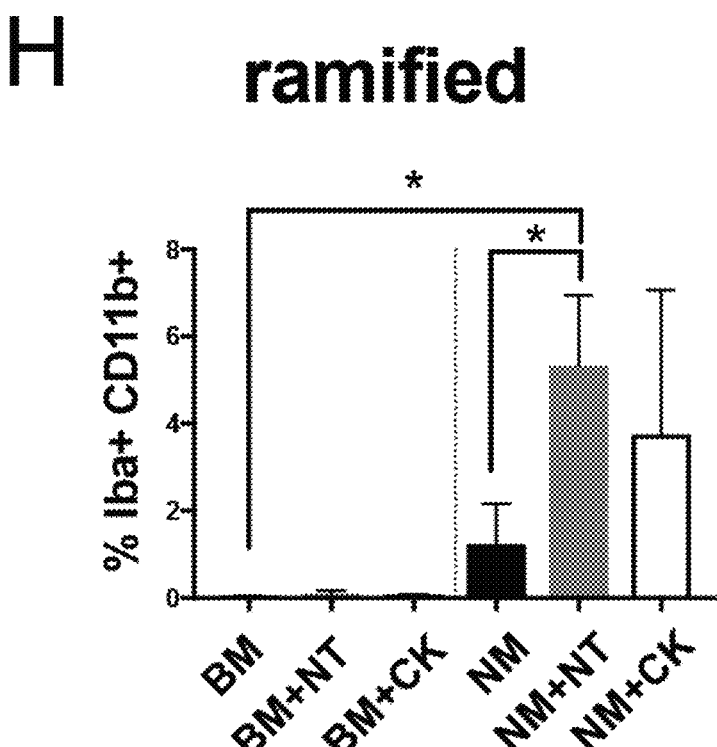
FIG. 4, cont.

NM CD11b+ 5 days, p6 and above

B.

NM+NT CD11b+ 5days, p6 and above

C.

NM+CK CD11b+ 5days, p6 and above

A.

B.
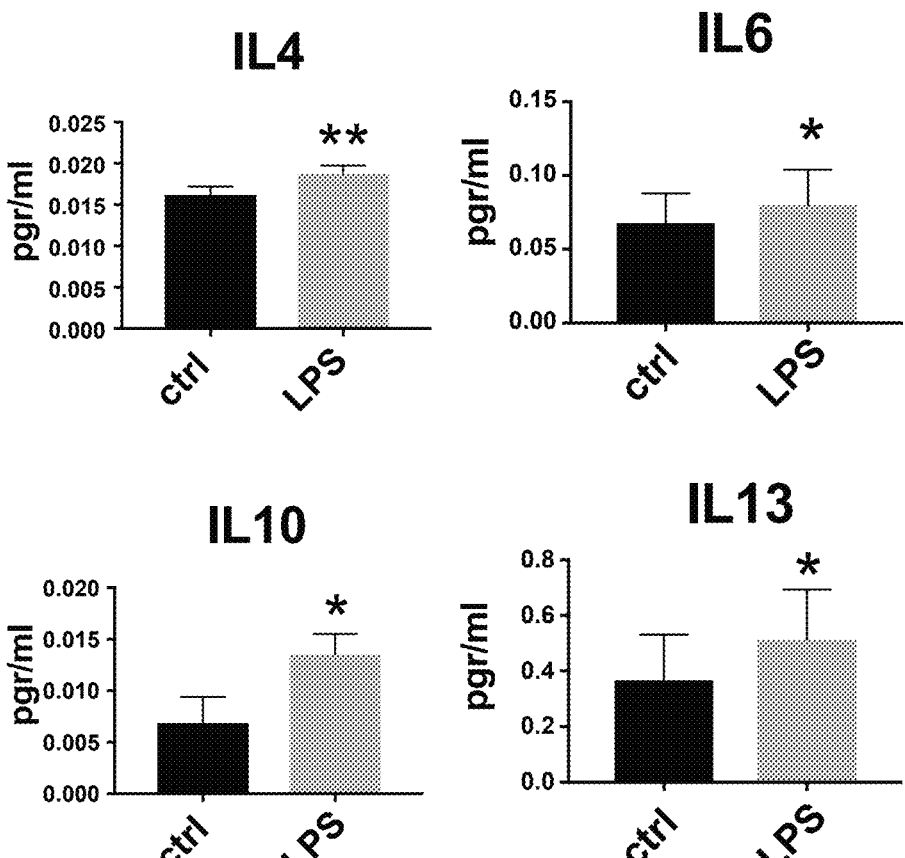
C.
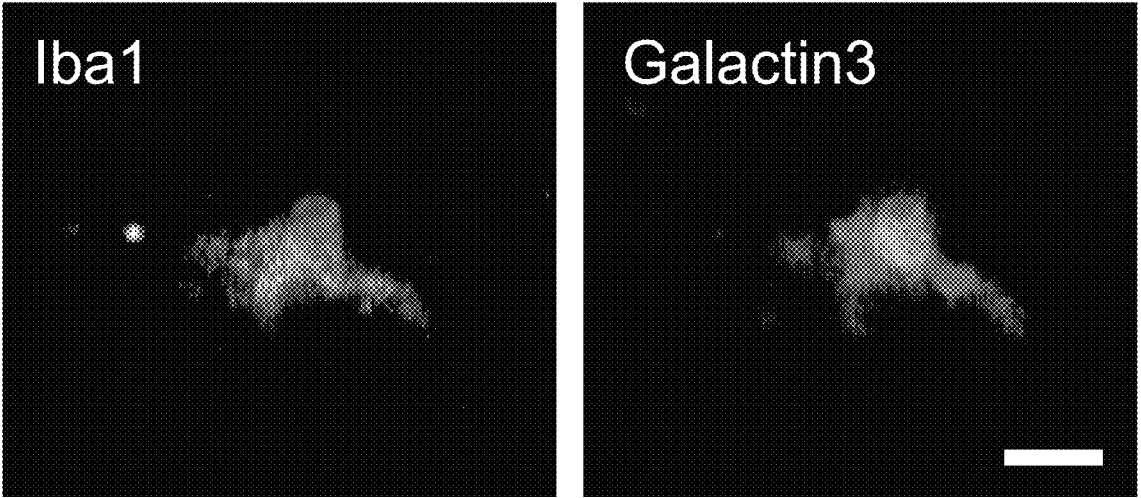
FIG. 8, cont.

BONE MARROW MICROGLIA PROGENITOR CELLS AND USES THEREOF

TECHNICAL FIELD

The present invention relates to microglia-like cells derived from bone marrow, and uses thereof, as well as methods for isolation.

BACKGROUND

Microglia, the Central Nervous System's (CNS) unique myeloid cells, are key players at the onset, development and progression of CNS pathologies, including intractable brain tumors like glioblastoma (GBM), neurodegenerative and psychiatric disorders. Likewise, microglia play a fundamental role in the correct brain development and function during ontogeny and adulthood.

To date, exploring therapies using human microglia-like cells are hampered due to a lack of 1) nervous system microglia sources and 2) fast and safe stem cell approaches for deriving microglia. Current methods using induced pluripotent cells are time-consuming ($>\frac{1}{2}$ year), associate with tumor risks and have low efficiency, thus making GBM treatment impossible. The use of embryonic stem cells carries ethical concerns and limited access.

There are several publications disclosing microglia cells or cell lines. Rahmat et al. 2013 discloses a murine immortalized, HLA-DR$^+$ and HLA-ABC$^+$ BV2 microglia cell line in co-culture with mesenchymal stem cells (MSCs). Another study discloses CD11b$^+$/CD45$^-$ enriched microglia cells from adult mouse brain (Nikodemova and Watters, 2012). It is also possible to differentiate other cells toward microglia-like cells, such as disclosed in Hinze and Stolzing (Hinze and Stolzing, 2011), where human bone marrow cells are differentiated toward CD11b$^+$/CD45$^+$ microglia-like cells. This is, however, a time-consuming procedure.

Accordingly, there is a need to develop methods for the rapid manufacture of pure, high quality microglia populations, which can be used in medical applications.

SUMMARY

The inventors have found the presence of a non-hematopoietic, non-mesenchymal cell population in the stroma compartment of the human bone marrow that shares the microglia genetic signature, named microglia progenitor cells.

The present disclosure provides stroma microglia as an in vitro model for human microglia, which can bypass current methodological drawbacks in cell replacement therapy methodologies. Furthermore, the present disclosure provides differentiated microglia cells more rapidly compared to prior art, see Example 8.

In one aspect, the present invention provides a method for manufacturing an enriched population of microglia cells, the method comprising the steps of:

a) providing a sample A and optionally a sample B, both comprising bone marrow stromal cells and/or placenta stromal cells and/or umbilical cord stromal cells;

b) isolating CD11b$^+$, CD45$^-$ microglia progenitor cells from sample A;

c) i) contacting sample B with a culturing media comprising serum, thereby expanding the bone marrow stromal cells and/or placenta stromal cells and/or umbilical cord stromal cells as mesenchymal stem cells (MSCs); or ii) providing MSCs;

d) contacting the CD11b$^+$, CD45$^-$ microglia progenitor cells of sample A, step (b), with the MSCs of step (c) to generate a sample C;

e) removing the media comprising serum from sample C;

f) contacting the serum free sample C of step (e) with a substantially serum free media comprising at least one growth factor; thereby expanding and differentiating the CD11b$^+$, CD45$^-$ microglia progenitor cells;

g) obtaining an enriched population of mature microglia cells.

In another aspect, the present invention provides an enriched population of microglia cells obtainable by the method according to the aspect above.

In one aspect, the present invention provides an in vitro method for determining the effect of at least one biological agent on microglia the method comprising:

a) providing a sample A and optionally a sample B comprising bone marrow stromal cells and/or placenta stromal cells and/or umbilical cord stromal cells;

b) isolating CD11b$^+$, CD45$^-$ microglia progenitor cells from sample A;

c) i) contacting sample B with a culturing media comprising serum, thereby expanding the bone marrow stromal cells and/or placenta stroma cells as mesenchymal stem cells (MSCs); or ii) providing MSCs;

d) contacting the CD11b$^+$, CD45$^-$ microglia progenitor cells of sample A, step (b), with the MSCs of step (c) to generate a sample C; thereby expanding and differentiating the CD11b$^+$, CD45$^-$ microglia progenitor cells;

e) removing the media comprising serum from sample C;

f) contacting the serum free sample C of step (e) with a substantially serum free media comprising at least one growth factor;

g) obtaining an enriched population of mature microglia cells;

h) contacting the enriched population of microglia cells with the biological agent; and i) determining the effect of the biological agent on microglia.

In another aspect, the present invention provides a method for determining genetic risk factors associated with disorders of the CNS and/or psychiatric disorders in a subject, the method comprising:

a) providing a sample A and optionally a sample B, both comprising bone marrow stromal cells and/or placenta stromal cells and/or umbilical cord stromal cells;

b) i) isolating CD11b$^+$, CD45$^-$ microglia progenitor cells from sample A;

or i') isolating CD11b$^+$, CD45$^-$ microglia progenitor cells from sample A;

ii') contacting sample B with a culturing media comprising serum, thereby differentiating the bone marrow stromal cells and/or placenta stromal cells and/or umbilical cord stromal cells into mesenchymal stem cells (MSCs); or iii') providing MSCs;

iv') contacting the CD11b$^+$, CD45$^-$ microglia progenitor cells of sample A, step (I'), with the MSCs of step (ii') or (iii') to generate a sample C;

v') removing the media comprising serum from sample C;

vi') contacting the serum free sample C of step (v') with a substantially serum free media comprising at least one growth factor; thereby expanding and differentiating the CD11b$^+$, CD45$^-$ microglia progenitor cells;

vii') obtaining an enriched population of microglia cells;

c) analyzing the gene expression of the isolated microglia progenitor cells or the microglia cells of step (b);

d) comparing the gene expression of step (c) with the gene expression of a reference cell population; and e) determining whether the subject has a gene expression associated with a disorder of the CNS and/or psychiatric disorders.

In one aspect, the present invention provides a method for determining biomarkers associated with disorders of the CNS and/or psychiatric disorders, the method comprising:

a) providing a sample A and optionally a sample B, both comprising bone marrow stromal cells and/or placenta stromal cells and/or umbilical cord stromal cells;

b) i) isolating CD11b$^+$, CD45$^-$ microglia progenitor cells from sample A;

or i') isolating CD11b$^+$, CD45$^-$ microglia progenitor cells from sample A;

ii') contacting sample B with a culturing media comprising serum, thereby expanding the bone marrow stromal cells and/or placenta stromal cells and/or umbilical cord stromal cells into mesenchymal stem cells (MSCs); or iii') providing MSCs;

iv') contacting the CD11b$^+$, CD45$^-$ microglia progenitor cells of sample A, step (I'), with the MSCs of step (ii') or (iii') to generate a sample C;

v') removing the media comprising serum from sample C;

vi') contacting the serum free sample C of step (v') with a substantially serum free media comprising at least one growth factor; thereby expanding and differentiating the CD11b$^+$, CD45$^-$ microglia progenitor cells;

vii') obtaining an enriched population of microglia cells;

c) analyzing the gene expression of the isolated microglia progenitor cells or the microglia cells of step (b);

d) comparing the gene expression of step (c) with the gene expression of a reference cell population; and e) determining whether a gene is associated with a disorder of the CNS and/or psychiatric disorder.

In another aspect, the present invention provides an in vitro cell culture of microglia progenitor cells, wherein a) the cells are derived from bone marrow and/or placenta stromal cells and/or umbilical cord stromal cells;

b) the cell culture is capable of proliferating in a culture medium containing serum;

c) the cells are cultured with mesenchymal stem cells;

d) the cells are CD11b$^+$ and CD45$^-$; and e) the cells in the culture have the capacity to differentiate into microglia in media upon withdrawal of serum and addition of at least one growth factor.

In another aspect, the present invention provides an enriched population of mammalian cells, wherein at least 50%, such as at least 60%, for example at least 70%, preferably at least 80%, more preferably at least 90% of the cells are CD11b$^+$ and CD45$^-$ microglia progenitor cells.

In yet another aspect, the present invention provides a composition comprising an enriched population of microglia cells and/or a cell culture according to the aspects above.

In one aspect, the present invention provides a method of providing an enriched population of microglia progenitor cells, the method comprising the steps of:

a) providing a sample A comprising bone marrow stromal cells and/or placenta stromal cells and/or umbilical cord stromal cells;

b) isolating CD11b$^+$, CD45$^-$, HLA-DR$^-$ microglia progenitor cells from sample A; and c) obtaining an enriched population of microglia progenitor cells.

In one aspect, the present invention provides an enriched population of microglia cells, a cell culture, or a composition according to any one of the above aspects, for use as a medicament.

In one aspect, the present invention provides an enriched population of microglia cells, a cell culture, or a composition according to any one of the above aspects, for use in the treatment of disorders of the CNS.

In one aspect, the present invention provides a method of treating disorders of the CNS in a patient in need thereof, the method comprising administering a therapeutically effective amount of an enriched population of microglia cells or a composition according to the above aspects.

In another aspect, the present invention provides a use of an enriched population of microglia progenitor cells, or a composition according to the above aspects, in the manufacture of a medicament for preventing or treating disorders of the CNS.

DESCRIPTION OF DRAWINGS

FIG. 5. Functional analysis of the non-hematopoietic CD11b$^+$ cells in non-aging and aging cultures. A. Graph showing the number of engulfed beads per Iba1$^+$ CD11b$^+$ cell in the aging cultures. An increase in the number of engulfed beads per cell increases when cultures are treated for 5 weeks in serum containing medium supplemented with CK. B. Detection of human TNF-α concentration in the supernatants of aging cultures under LPS-exposure and control (vehicle) conditions at the 5 week time point. Representative graph that applies also to non-aging cultures. Note that the number of CD11b$^+$ cells present in the wells were not controlled and a fold change cannot be extrapolated. C. Graph showing fold change in the intensities for CD40 expression in CD11b$^+$ cells as an indirect measure of CD40 increased expression after LPS treatment in aging cultures at the 5 week time point. NM: neuronal medium, a.k.a. expansion medium. NM+NT: neuronal medium supplemented with neurotrophins. NM+CK: neuronal medium supplemented with cytokines.

DETAILED DESCRIPTION

The Method

Figure 1:
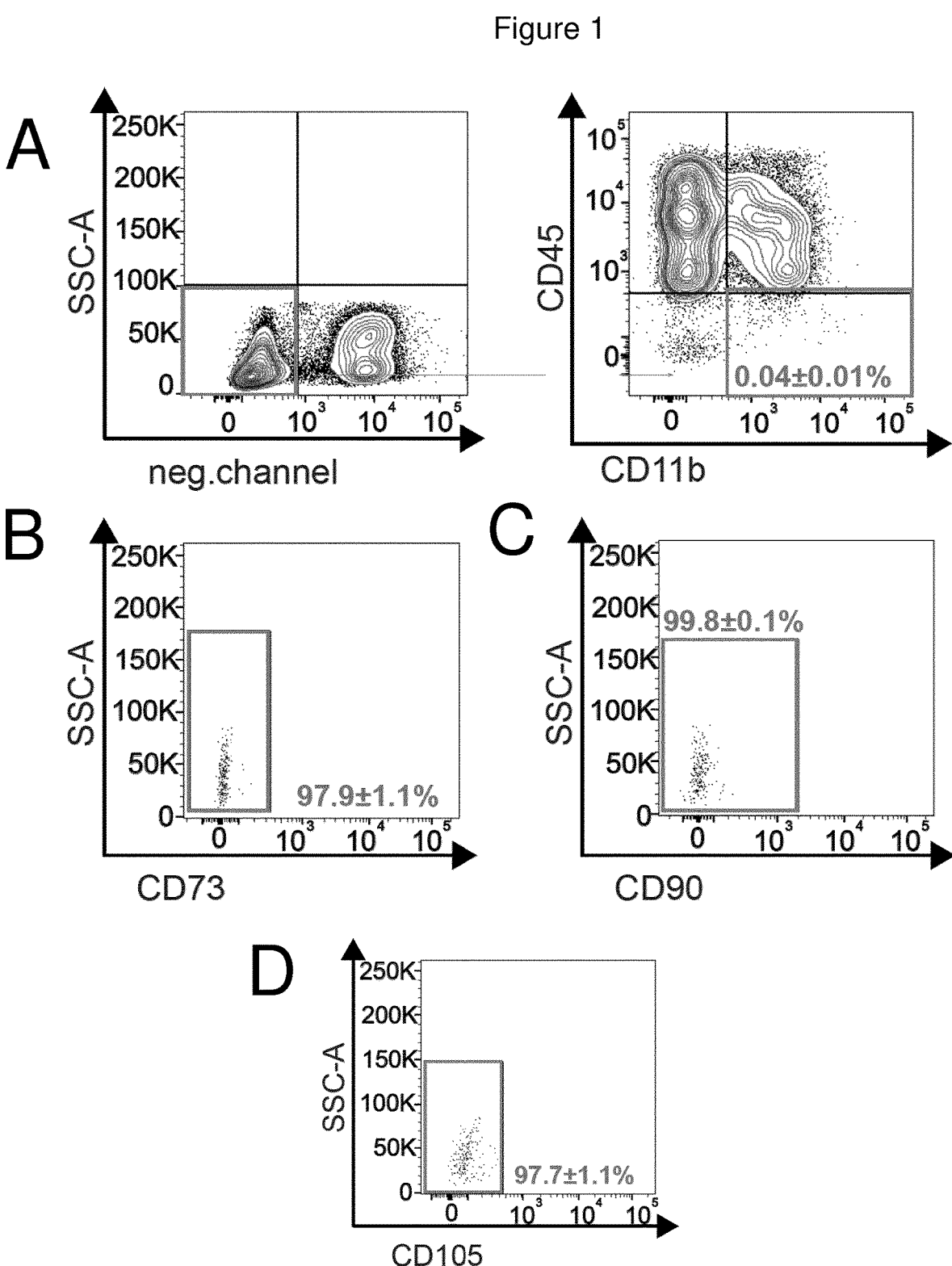
FIG. 1. Human bone marrow stromal cells harbor non-hematopoietic CD11b$^+$ cells with a microglial gene expression panel. A-D Representative case showing the gating strategy for detecting non-hematopoietic CD11b$^+$ cells. Within the compartment for alive cells negative to markers to label endothelial and hematopoietic lineages and hematopoietic stem cells, negative cells to CD45 but positive for CD11b cells were selected. Within this compartment, resulted cells were analyzed for CD90, CD73 and CD105 mesenchymal markers.

The present invention provides a method for manufacturing an enriched population of microglia cells. The method relates to the isolation of microglia progenitor cells, their expansion and differentiation into microglia. These cells can be beneficial for treatment of disorders of the CNS such as glioblastoma. Furthermore, the methods can be applied to determine the effect of a biological agent on said enriched population of microglia cells, and to determine genetic risk factors associated with disorders of the CNS and/or psychiatric disorders.

The term STR-MP, as used herein, refer to stroma microglia progenitor cells, and can also be referred to as TRM progenitors. The term STR-M, as used herein, refers to the mature stroma microglia cells. Furthermore, mesenchymal stem cells (MSCs), are multipotent stromal cells than can differentiate into a variety of cell types, such as osteoblasts, chondrocytes, myocytes, adipocytes and microglia cells. MSCs can be found in various tissues of the body, including bone marrow, placenta, umbilical cord and adipose tissue.

In one aspect, the present invention provides a method for manufacturing an enriched population of microglia cells, the method comprising the steps of:
  a) providing a sample A and optionally a sample B, both comprising bone marrow stromal cells and/or placenta stromal cells and/or umbilical cord stromal cells;
  b) isolating CD11b$^+$, CD45$^-$ microglia progenitor cells from sample A;
  c) i) contacting sample B with a culturing media comprising serum, thereby expanding the bone marrow stromal cells and/or placenta stromal cells and/or umbilical cord stromal cells into mesenchymal stem cells (MSCs); or ii) providing MSCs;

d) contacting the CD11b$^+$, CD45$^-$ microglia progenitor cells of sample A, step (b), with the MSCs of step (c) to generate a sample C;

e) removing the media comprising serum from sample C;

f) contacting the serum free sample C of step (e) with a substantially serum free media comprising at least one growth factor; thereby expanding and differentiating the CD11b$^+$, CD45$^-$ microglia progenitor cells;

g) obtaining an enriched population of microglia cells.

In one embodiment, the present invention provides a method for manufacturing an enriched population of microglia cells, the method comprising the steps of:

a) providing a sample A comprising bone marrow stromal cells and/or placenta stromal cells and/or umbilical cord stromal cells;

b) isolating CD11b$^+$, CD45$^-$ microglia progenitor cells from sample A;

c) providing MSCs;

d) contacting the CD11b$^+$, CD45$^-$ microglia progenitor cells of sample A, step (b), with the MSCs of step (c) to generate a sample C;

e) removing the media comprising serum from sample C;

f) contacting the serum free sample C of step (e) with a substantially serum free media comprising at least one growth factor; thereby expanding and differentiating the CD11b$^+$, CD45$^-$ microglia progenitor cells;

g) obtaining an enriched population of microglia cells.

In one embodiment, the present invention provides a method for manufacturing an enriched population of microglia cells, the method comprising the steps of:

a) providing a sample A and a sample B, both comprising bone marrow stromal cells and/or placenta stromal cells and/or umbilical cord stromal cells;

b) isolating CD11b$^+$, CD45$^-$ microglia progenitor cells from sample A;

c) contacting sample B with a culturing media comprising serum, thereby expanding the bone marrow stromal cells and/or placenta stromal cells and/or umbilical cord stromal cells into mesenchymal stem cells (MSCs);

d) contacting the CD11b$^+$, CD45$^-$ microglia progenitor cells of sample A, step (b), with the MSCs of step (c) to generate a sample C;

e) removing the media comprising serum from sample C;

f) contacting the serum free sample C of step (e) with a substantially serum free media comprising at least one growth factor; thereby expanding and differentiating the CD11b$^+$, CD45$^-$ microglia progenitor cells; and g) obtaining an enriched population of microglia cells.

In another aspect, the present invention provides an enriched population of microglia cells obtainable by the method according to the above aspect and embodiments.

The obtained enriched population of microglia progenitor cells, can be expanded, frozen and stored, or differentiated into mature microglia cells.

In one aspect, the present invention provides an in vitro method for determining the effect of at least one biological agent on a microglia the method comprising:

a) providing a sample A and optionally a sample B, both comprising bone marrow stromal cells and/or placenta stromal cells and/or umbilical cord stromal cells;

b) isolating CD11b$^+$, CD45$^-$ microglia progenitor cells from sample A;

c) i) contacting sample B with a culturing media comprising serum, thereby expanding the bone marrow stromal cells and/or placenta stromal cells and/or umbilical cord stromal cells into mesenchymal stem cells (MSCs); or ii) providing MSCs;

d) contacting the CD11b$^+$, CD45$^-$ microglia progenitor cells of sample A, step (b), with the MSCs of step (c) to generate a sample C; thereby expanding and differentiating the CD11b$^+$, CD45$^-$ microglia progenitor cells;

e) removing the media comprising serum from sample C;

f) contacting the serum free sample C of step (e) with a substantially serum free media comprising at least one growth factor;

g) obtaining an enriched population of microglia cells;

h) contacting the enriched population of microglia cells with the biological agent; and i) determining the effect of the biological agent on microglia.

In one embodiment, the present invention provides an in vitro method for determining the effect of at least one biological agent on a microglia the method comprising:

a) providing a sample A and optionally a sample B, both comprising bone marrow stromal cells and/or placenta stromal cells and/or umbilical cord stromal cells;

b) isolating CD11b$^+$, CD45$^-$ microglia progenitor cells from sample A;

c) contacting sample B with a culturing media comprising serum, thereby expanding the bone marrow stromal cells and/or placenta stromal cells and/or umbilical cord stromal cells into mesenchymal stem cells (MSCs);

d) contacting the CD11b$^+$, CD45$^-$ microglia progenitor cells of sample A, step (b), with the MSCs of step (c) to generate a sample C; thereby expanding and differentiating the CD11b$^+$, CD45$^-$ microglia progenitor cells;

e) removing the media comprising serum from sample C;

f) contacting the serum free sample C of step (e) with a substantially serum free media comprising at least one growth factor;

g) obtaining an enriched population of microglia cells;

h) contacting the enriched population of microglia cells with the biological agent; and i) determining the effect of the biological agent on microglia.

In one embodiment, the present invention provides an in vitro method for determining the effect of at least one biological agent on a microglia the method comprising:

a) providing a sample A comprising bone marrow stromal cells and/or placenta stromal cells and/or umbilical cord stromal cells;

b) isolating CD11b$^+$, CD45$^-$ microglia progenitor cells from sample A;

c) providing MSCs;

d) contacting the CD11b$^+$, CD45$^-$ microglia progenitor cells of sample A, step (b), with the MSCs of step (c) to generate a sample C; thereby expanding and differentiating the CD11b$^+$, CD45$^-$ microglia progenitor cells;

e) removing the media comprising serum from sample C;

f) contacting the serum free sample C of step (e) with a substantially serum free media comprising at least one growth factor;

9 | 10 g) obtaining an enriched population of microglia cells;

h) contacting the enriched population of microglia cells with the biological agent; and i) determining the effect of the biological agent on microglia.

In one embodiment, the substantially serum free media further comprises at least one cytokine.

In one embodiment, the present invention provides a method for manufacturing an enriched population of microglia cells, the method comprising the steps of:

a) providing a sample A and optionally a sample B, both comprising bone marrow stromal cells and/or placenta stromal cells and/or umbilical cord stromal cells;

b) isolating CD11b$^+$, CD45$^-$ microglia progenitor cells from sample A;

c) i) contacting sample B with a culturing media comprising serum, thereby expanding the bone marrow stromal cells and/or placenta stromal cells and/or umbilical cord stromal cells as mesenchymal stem cells (MSCs); or ii) providing MSCs;

d) contacting the CD11b$^+$, CD45$^-$ microglia progenitor cells of sample A, step (b), with the MSCs of step (c) to generate a sample C;

e) culturing the cells in sample C; thereby obtaining an expanded population of CD11b$^+$, CD45$^-$ microglia progenitor cells.

In one embodiment, the present invention provides an in vitro method for determining the effect of at least one biological agent on a microglia the method comprising:

a) providing a sample A and optionally a sample B comprising bone marrow stromal cells and/or placenta stromal cells and/or umbilical cord stromal cells;

b) isolating CD11b$^+$, CD45$^-$ microglia progenitor cells from sample A;

c) i) contacting sample B with a culturing media comprising serum, thereby expanding the bone marrow stromal cells and/or placenta stroma cells as mesenchymal stem cells (MSCs); or ii) providing MSCs;

d) contacting the CD11b$^+$, CD45$^-$ microglia progenitor cells of sample A, step (b), with the MSCs of step (c) to generate a sample C; thereby expanding and the CD11b$^+$, CD45$^-$ microglia progenitor cells;

e) culturing the cells in sample C; thereby obtaining an expanded population of CD11b$^+$, CD45$^-$ microglia progenitor cells;

f) contacting the expanded population of CD11b$^+$, CD45$^-$ microglia progenitor cells of step (e) with the biological agent; and g) determining the effect of the biological agent on the microglia progenitor cells.

In one embodiment, the present invention provides CD11b$^+$, CD45$^-$ microglia progenitor cells for use as a medicament. In one embodiment, the present invention provides CD11b$^+$, CD45$^-$ microglia progenitor cells for use in the treatment of disorders of the CNS.

In another embodiment, the present invention provides CD11b$^+$, CD45$^-$ microglia progenitor cells, wherein the microglia cells are negative for one or more markers selected from the group consisting of CD73, CD90, CD105, HLA-DR, CD14, CD19, CD34 and HLA-ABC.

In one embodiment, the enriched population of microglia cells is in the amount of at least 0.5 million cells, such as at least 1 million cells, for example at least 1.5 million cells, such as at least 2 million cells, for example at least 2.5 million cells, such as at least 3 million cells, for example at least 3.5 million cells, such as at least 4 million cells, for example at least 4.5 million cells, such as at least 5 million cells. In one embodiment, the enriched population of microglia cells is in the amount of at least 5.5 million cells, such as at least 6 million cells, for example at least 6.5 million cells.

In one embodiment, the enriched population of CD11b$^+$, CD45$^-$ microglia progenitor cells is in the amount of at least 0.5 million cells, such as at least 1 million cells, for example at least 1.5 million cells, such as at least 2 million cells, for example at least 2.5 million cells, such as at least 3 million cells, for example at least 3.5 million cells, such as at least 4 million cells, for example at least 4.5 million cells, such as at least 5 million cells. In one embodiment, the enriched population of CD11b$^+$, CD45$^-$ microglia progenitor cells is in the amount of at least 5.5 million cells, such as at least 6 million cells, for example at least 6.5 million cells.

In one embodiment, the biological agent is selected from the group consisting of growth factors, trophic factors, growth factor receptors, neurotransmitters, neuropeptides, neurotrophic factors, hormones, enzymes, cytokines, lymphokines, anti-angiogenic factors, transcription factors, proliferation factors and antibodies.

In one aspect, the present invention provides a method for determining genetic risk factors associated with disorders of the CNS and/or psychiatric disorders in a subject, the method comprising:

a) providing a sample A and optionally a sample B, both comprising bone marrow stromal cells and/or placenta stromal cells and/or umbilical cord stromal cells;

b) i) isolating CD11b$^+$, CD45$^-$ microglia progenitor cells from sample A;

or i') isolating CD11b$^+$, CD45$^-$ microglia progenitor cells from sample A;

ii') contacting sample B with a culturing media comprising serum, thereby expanding the bone marrow stromal cells and/or placenta stroma cells into mesenchymal stem cells (MSCs); or iii') providing MSCs;

iv') contacting the CD11b$^+$, CD45$^-$ microglia progenitor cells of sample A, step (I'), with the MSCs of step (ii') or (iii') to generate a sample C;

v') removing the media comprising serum from sample C;

vi') contacting the serum free sample C of step (v') with a substantially serum free media comprising at least one growth factor; thereby expanding and differentiating the CD11b$^+$, CD45$^-$ microglia progenitor cells;

vii') obtaining an enriched population of microglia cells;

c) analyzing the gene expression of the isolated microglia progenitor cells or the microglia cells of step (b);

d) comparing the gene expression of step (c) with the gene expression of a reference cell population; and e) determining whether the subject has a gene expression associated with a disorder of the CNS and/or psychiatric disorders.

In another embodiment, the present invention provides a method for determining biomarkers associated with disorders of the CNS and/or psychiatric disorders, the method comprising:

a) providing a sample A comprising bone marrow stromal cells and/or placenta stromal cells and/or umbilical cord stromal cells;

b) isolating CD11b$^+$, CD45$^-$ microglia progenitor cells from sample A;

c) analyzing the gene expression of the isolated microglia progenitor cells or the microglia cells of step (b);

d) comparing the gene expression of step (c) with the gene expression of a reference cell population; and e) determining whether a gene is associated with a disorder of the CNS and/or psychiatric disorder.

In one embodiment, the present invention provides a method for determining genetic risk factors associated with disorders of the CNS and/or psychiatric disorders in a subject, the method comprising:

a) providing a sample A and a sample B, both comprising bone marrow stromal cells and/or placenta stromal cells and/or umbilical cord stromal cells;

b) i) isolating CD11b$^+$, CD45$^-$ microglia progenitor cells from sample A;

ii) contacting sample B with a culturing media comprising serum, thereby differentiating the bone marrow stromal cells and/or placenta stroma cells into mesenchymal stem cells (MSCs);

iii) contacting the CD11b$^+$, CD45$^-$ microglia progenitor cells of sample A, step (i), with the MSCs of step (ii) to generate a sample C;

iv) removing the media comprising serum from sample C;

v) contacting the serum free sample C of step (iv) with a substantially serum free media comprising at least one growth factor; thereby expanding and differentiating the CD11b$^+$, CD45$^-$ microglia progenitor cells;

vi) obtaining an enriched population of microglia cells;

c) analyzing the gene expression of the microglia cells of step (b);

d) comparing the gene expression of step (c) with the gene expression of a reference cell population; and e) determining whether the subject has a gene expression associated with a disorder of the CNS and/or psychiatric disorders.

The terms "isolating" as used herein refer to the action of identifying a cell as being a certain type of cell and separating it from cells that do not belong to the same cell type or to a differentiation state.

The term "substantially free from" is herein intended to mean below detection limits of the assay used thereby appearing negative, i.e. free from.

The isolation may be performed by various methods, e.g. any immune method known to the skilled man in the art, such as magnetic-activated cell sorting (MACS) or flow cytometry methods, e.g. fluorescence activated cell sorting (FACS).

Accordingly, in some embodiments, the expression of markers by a cell such as but not limited to CD11b, CD45 and Iba1 is detected via an antibody, wherein the antibody is a monoclonal antibody, polyclonal antibody, a chimeric antibody, a single chain antibody or fragment thereof.

In one embodiment, the reference cell population is a cell population derived from a healthy individual.

In one embodiment, the gene expression of the reference population has been obtained by said method.

In one embodiment, the growth factor is a neurotrophin or a glial cell line-derived neurotrophic factor (GDNF).

In one embodiment, the neurotrophin is selected from the group consisting of brain-derived neurotrophic factor (BDNF), nerve growth factor (NGF), neurotrophin-3 (NT-3) and neurotrophic 4 (NT-4).

In one embodiment, the cytokine is selected from the group consisting of M-CSF, IL34, TGF-beta CX3CL1 and CD200.

The person skilled in the art would understand that a cytokine may be a growth factor.

In one embodiment, the method for obtaining the enriched microglia cells takes no more than 1 week, such as no more than 2 weeks, for example no more than 3 weeks, such as for example no more than 4 weeks, such as no more than 5 weeks.

In one embodiment, the isolation of CD11b$^+$ and CD45$^-$ microglia progenitor cells takes no more than 24 hours, for example no more than 12 hours, such as no more than 6 hours.

In one embodiment, the expansion of the CD11b$^+$ and CD45$^-$ microglia progenitor cells takes no more than 2 weeks, for example no more than one week, for example no more than 5 days.

In one embodiment, the method to obtain an enriched population of microglia cells takes no more than 3 weeks, for example no more than 2 weeks, such as no more than 1 week, such as no more than 5 days.

In one embodiment, the present invention provides a method of providing an enriched population of microglia cells, the method comprising the steps of:

a) providing a sample A comprising bone marrow stromal cells and/or placenta stromal cells and/or umbilical cord stromal cells;

b) isolating CD11b$^+$, CD45$^-$, HLA-DR$^-$ microglia progenitor cells from sample A; and c) obtaining an enriched population of microglia progenitor cells.

Thus, in one embodiment, the microglia progenitor cells are CD11b$^+$, CD45$^-$ and HLA-DR$^-$.

In a preferred embodiment, at least 50%, 55%, 60%, 65%, 70%, such as at least 71%, 72%, 73%, 74%, 75%, 76%, 77%, 78%, 79%, preferably 80% of said microglia progenitor cells are HLA-ABC$^-$.

In another embodiment, the present invention provides a method of providing an enriched population of microglia progenitor cells, the method comprising the steps of:

a) providing a sample A comprising bone marrow stromal cells and/or placenta stromal cells and/or umbilical cord stromal cells;

b) isolating CD11b$^+$, CD45$^-$, HLA-ABC$^-$ microglia progenitor cells from sample A; and c) obtaining an enriched population of microglia progenitor cells.

Thus, in one embodiment, the microglia progenitor cells are CD11b$^+$, CD45$^-$ and HLA-ABC$^-$.

In yet another embodiment, the present invention provides a method of providing an enriched population of microglia progenitor cells, the method comprising the steps of:

a) providing a sample A comprising bone marrow stromal cells and/or placenta stromal cells and/or umbilical cord stromal cells;

b) isolating CD11b$^+$, CD45$^-$ HLA-DR HLA-ABC$^-$ microglia progenitor cells from sample A; and c) obtaining an enriched population of microglia progenitor cells.

Thus, in one embodiment, the microglia progenitor cells are $CD11b^+$, $CD45^-$ and $HLA-ABC^-$ and $HLA-DR^-$.

In Vitro Cell Culture

In one aspect, the present invention provides an in vitro cell culture of microglia progenitor cells, wherein a) the cells are derived from bone marrow and/or placenta stromal cells and/or umbilical cord stromal cells;

b) the cell culture is capable of proliferating in a culture medium containing serum;

c) the cells are cultured with mesenchymal stem cells;

d) the cells are $CD11b^+$ and $CD45^-$; and e) the cells in the culture have the capacity to differentiate into microglia in media upon withdrawal of serum and addition of at least one growth factor.

In one embodiment, at least 50%, 55%, 60%, 65%, 70%, such as at least 71%, 72%, 73%, 74%, 75%, 76%, 77%, 78%, 79%, preferably 80% of the cells in the culture are $HLA-DR^-$. The cells may also be $HLA-ABC^-$.

In one embodiment, at least 50%, 55%, 60%, 65%, 70%, such as at least 71%, 72%, 73%, 74%, 75%, 76%, 77%, 78%, 79%, preferably 80% of the cells in culture are $HLA-ABC^-$. In another embodiment, the cells in culture are $CD11b^+$, $CD45^-$ and $HLA-ABC^-$. In another embodiment, the cells in culture are $CD11b^+$, $CD45^-$ and $HLA-ABC^-$ and $HLA-DR^-$.

In one embodiment, the cells in the culture are negative for one or more markers selected from the group consisting of CD73, CD90, CD105, HLA-DR, CD14, CD19, CD34 and HLA-ABC.

In one embodiment, the cells in the culture are $CD73^-$. In one embodiment, the cells in the culture are $CD90^-$. In one embodiment, the cells in the culture are $CD105^-$. In one embodiment, the cells in the culture are $CD73^-$, $CD90^-$ and/or $CD105^-$.

In one embodiment, the cells in the culture are $HLA-DR^-$. In one embodiment, the cells in the culture are $CD14^-$. In one embodiment, the cells in the culture are $CD19^-$. In one embodiment, the cells in the culture are $CD34^-$. In one embodiment, the cells in the culture are $HLA-DR^-$, $CD14^-$, $CD19^-$ and/or $CD34^-$.

In one embodiment, the cells in the culture are $CD73^-$, $CD90^-$, $CD105^-$ and/or $HLA-DR^-$. In one embodiment, the cells in the culture are $CD73^-$, $CD90^-$, $CD105^-$, $HLA-DR^-$ and/or $CD14^-$. In one embodiment, the cells in the culture are $CD73^-$, $CD90^-$, $CD105^-$, $HLA-DR^-$, $CD14^-$ and/or $CD19^-$. In one embodiment, the cells in the culture are $CD73^-$, $CD90^-$, $CD105^-$, $HLA-DR^-$, $CD14^-$, $CD19^-$ and/or $CD34^-$.

In one embodiment, the cells in the culture are $CD73^-$, $CD90^-$, $CD105^-$ and/or $CD14^-$. In one embodiment, the cells in the culture are $CD73^-$, $CD90^-$, $CD105^-$, $CD14^-$ and/or $CD19^-$. In one embodiment, the cells in the culture are $CD73^-$, $CD90^-$, $CD105^-$, $CD14^-$ $CD19^-$ and/or $CD34^-$.

In one embodiment, the cells in the culture are $CD73^-$, $CD90^-$, $CD105^-$ and/or $CD19^-$. In one embodiment, the cells in the culture are $CD73^-$, $CD90^-$, $CD105^-$, $CD19^-$ and/or $HLA-DR^-$. In one embodiment, the cells in the culture are $CD73^-$, $CD90^-$, $CD105^-$, $CD19^-$, $CD34^-$ and/or $HLA-DR^-$.

In one embodiment, the cells in the culture are $CD73^-$, $CD90^-$, $CD105^-$ and/or $CD34^-$. In one embodiment, the cells in the culture are $CD73^-$, $CD90^-$, $CD105^-$, $CD34^-$ and/or $HLA-DR^-$. In one embodiment, the cells in the culture are $CD73^-$, $CD90^-$, $CD105^-$, $CD34^-$ and/or $CD14^-$. In one embodiment, the cells in the culture are $CD73^-$, $CD90^-$, $CD105^-$, $CD34^-$ and/or $CD19^-$.

In one embodiment, the media further comprises at least one cytokine.

In one embodiment, the culture is capable of at least 6 doublings, such as at least 12 doublings, for example at least 18 doublings.

In one embodiment, the cells in the culture are mammalian cells. In one embodiment, the cells in the culture are human cells. In one embodiment, the cells in the culture are murine cells. In one embodiment, the cells in the culture are rat cells.

The Microglia Progenitor Cells

Microglia progenitor cells refer to cells capable of differentiating into mature microglia. Thus $CD11b^+$ $CD45^-$ microglia progenitor cells can differentiate into mature microglia. Stroma microglia refers to mature microglia that are derived from microglial progenitor cells originated from the stroma.

In one aspect, the present invention provides an enriched population of mammalian cells, wherein at least 50%, such as at least 60%, for example at least 70%, preferably at least 80%, more preferably at least 90% of the cells are $CD11b^+$ and $CD45^-$ microglia progenitor cells.

In one embodiment, the present invention provides an enriched population of mammalian cells, wherein at least 95%, such as at least 96%, for example at least 97%, such as at least 98%, for example 99% of the cells are $CD11b^+$ and $CD45^-$ microglia progenitor cells.

In one embodiment, the enriched population of mammalian cells is derived from bone marrow. In on embodiment, the enriched population of mammalian cells are derived from placenta cells. In on embodiment, the enriched population of mammalian cells are derived from bone marrow and/or placenta cells and/or umbilical cord stromal cells. In one embodiment, he enriched population of mammalian cells are derived from umbilical cord stromal cells. In another embodiment, at least 50%, 55%, 60%, 65%, 70%, such as at least 71%, 72%, 73%, 74%, 75%, 76%, 77%, 78%, 79%, preferably 80% of the enriched population of mammalian cells are $HLA-DR^-$.

In another embodiment, the microglia progenitor cells are $CD11b^+$, $CD45^-$ and $HLA-DR^-$. In yet another embodiment, the microglia progenitor cells are $CD11b^+$, $CD45^-$ and $HLA-ABC^-$. In another embodiment, the microglia progenitor cells are $CD11b^+$, $CD45^-$ and $HLA-ABC^-$ and $HLA-DR^-$. In one embodiment, the microglia progenitor cells are negative for one or more markers selected from the group consisting of CD73, CD90, CD105, HLA-DR, CD14, CD19, CD34 and HLA-ABC.

In one embodiment, the microglia progenitor cells are $CD73^-$. In one embodiment, the microglia progenitor cells are $CD90^-$. In one embodiment, the microglia progenitor cells are $CD105^-$. In one embodiment, the microglia progenitor cells are $CD73^-$, $CD90^-$ and/or $CD105^-$.

In one embodiment, the microglia progenitor cells are $HLA-DR^-$. In one embodiment, the microglia progenitor cells are $CD14^-$. In one embodiment, the microglia progenitor cells are $CD19^-$. In one embodiment, the microglia progenitor cells are $CD34^-$. In one embodiment, the microglia progenitor cells are $HLA-DR^-$, $CD14^-$, $CD19^-$ and/or $CD34^-$.

In one embodiment, the microglia progenitor cells are $CD73^-$, $CD90^-$, $CD105^-$ and/or $HLA-DR^-$. In one embodiment, the microglia progenitor cells are $CD73^-$, $CD90^-$, $CD105^-$, $HLA-DR^-$ and/or $CD14^-$. In one embodiment, the microglia progenitor cells are $CD73^-$, $CD90^-$, $CD105^-$, $HLA-DR^-$, $CD14^-$ and/or $CD19^-$. In one embodiment, the microglia progenitor cells are CD73⁻, CD90⁻, CD105⁻, HLA-DR⁻, CD14⁻, CD19⁻ and/or CD34⁻.

In one embodiment, the microglia progenitor cells are CD73⁻, CD90⁻, CD105⁻ and/or CD14⁻. In one embodiment, the microglia progenitor cells are CD73⁻, CD90⁻, CD105⁻, CD14⁻ and/or CD19⁻. In one embodiment, the microglia progenitor cells are CD73⁻, CD90⁻, CD105⁻, CD14⁻ CD19⁻ and/or CD34⁻.

In one embodiment, the microglia progenitor cells are CD73⁻, CD90⁻, CD105⁻ and/or CD19⁻. In one embodiment, the microglia progenitor cells are CD73⁻, CD90⁻, CD105⁻, CD19⁻ and/or HLA-DR⁻. In one embodiment, the microglia progenitor cells are CD73⁻, CD90⁻, CD105⁻, CD19⁻, CD34⁻ and/or HLA-DR⁻.

In one embodiment, the microglia progenitor cells are CD73⁻, CD90⁻, CD105⁻ and/or CD34⁻. In one embodiment, the microglia progenitor cells are CD73⁻, CD90⁻, CD105⁻, CD34⁻ and/or HLA-DR⁻. In one embodiment, the microglia progenitor cells are CD73⁻, CD90⁻, CD105⁻, CD34⁻ and/or CD14⁻. In one embodiment, the microglia progenitor cells are CD73⁻, CD90⁻, CD105⁻, CD34⁻ and/or CD19⁻.

In one embodiment, the microglia progenitor cells are CD11b⁺ and CD45 low.

In one embodiment, the microglia progenitor cells express genes selected from the group consisting of TMEM119, MERTK1, GPR34, ENTPD1, CX3CR1, Iba1, P2RY12, GPR34, C1QA, PROS1, CD33, GPR56, CABLES1, BHLHE41, TMEM119, TGFBR1, ENTPD1, ITGB2, ITGAM, AIF, IRF8, ADORA3 and PPARD.

In one embodiment, the microglia progenitor cells are TMEM119⁺, CX3CR1⁺, CD33⁺, TGFBR1⁺ and/or ITGAM⁺.

In one embodiment, the microglia progenitor cells express transcription factors selected from the group consisting of RUNX1, PU.1 and CSF1 R.

In one embodiment, the microglia progenitor cells are CD73⁻, CD90⁻ and/or CD105⁻.

In one embodiment, the enriched population of mammalian cells do not comprise hematopoietic stem cells. In one embodiment, the enriched population of mammalian cells do not comprise mesenchymal stem cells.

In one embodiment, at least some of the cells in culture are capable of differentiating into microglia in the absence of serum from the culture medium.

In one embodiment, the morphology of the differentiated microglia is semi-ramified or ramified.

In one embodiment, the enriched population of mammalian cells are phagocytes.

In one embodiment, the enriched population of microglia cells are phagocytes.

In one embodiment, the enriched population of mammalian cells are polarized. In one embodiment, the enriched population of microglia cells are polarized.

In one embodiment, the microglia progenitor cells express Iba1.

In one embodiment, the microglia progenitor cells can differentiate into mature microglia.

In one embodiment, the mammalian cells are human cells. In on embodiment, the mammalian cells are murine cells.

In one embodiment, the microglia progenitor cells attach to plastic.

The Composition

In one aspect, the present invention provides a composition comprising an enriched population of microglia cells and/or a cell culture according to the above aspects.

In one embodiment, the composition is a pharmaceutical composition.

In one embodiment, the composition further comprises an agent.

In one embodiment, the agent is an immunotherapeutic agent or a chemotherapeutic agent.

In one embodiment, the present invention provides a composition comprising CD11b⁺, CD45⁻ microglia progenitor cells.

Disorders of the Central Nervous System (CNS) and Psychiatric Disorder

In one aspect, the present invention provides an enriched population of microglia cells, a cell culture, or a composition according to the aspects above, for use as a medicament.

In one aspect, the present invention provides an enriched population of microglia cells, a cell culture, or a composition according to the aspects above, for use in the treatment of disorders of the CNS.

In one aspect, the present invention provides an enriched population of microglia cells, a cell culture, or a composition according to the aspects above, for use in the treatment of psychiatric disorders.

In one embodiment, the disorder of the CNS is selected from the group consisting of a neurodegenerative disorder, a brain tumor and stroke. In one embodiment, the brain tumor is glioblastoma. In one embodiment, the disorder of the CNS is selected from the group consisting of Alzheimer's disease, Parkinson's disease, multiple sclerosis, brain tumor and stroke.

In one embodiment, the neurodegenerative disorder is selected from the group consisting of Alzheimer's disease, Parkinson's disease and multiple sclerosis.

In one embodiment, the psychiatric disorder is a neurodevelopmental psychiatric disorder.

In one embodiment, the neurodevelopmental psychiatric disorder is selected form the group consisting of nasu-hakola disease, hereditary diffuse leukoencephaly with spheroids, rett syndrome, William's Syndrome, autism spectrum disorders and obsessive-compulsive disorder.

In one embodiment, the psychiatric disorder is an adult neuropsychiatric disorder.

In one embodiment, the adult neuropsychiatric disorder is selected from the group consisting of alcohol abuse, drug abuse, depressive disorder, schizophrenia, bipolar disorder, eating disorder and sleep disorder.

In one aspect, the present invention provides a method of treating disorders of the CNS in a patient in need thereof, the method comprising administering a therapeutically effective amount of an enriched population of microglia cells, or a composition according to the above aspects.

In one embodiment, the present invention provides a method of treating disorders of the CNS in a patient in need thereof, the method comprising administering a therapeutically effective amount of an enriched population of microglia progenitor cells according to the above aspects.

In one embodiment, the patient is a human.

An "effective amount" or "therapeutically effective amount" of an enriched population of microglia cells is that amount of cells which is sufficient to provide a beneficial effect to the subject to which the compound is administered.

In one aspect, the present invention provides a use of an enriched population of microglia progenitor cells, or a composition according to the above aspects, in the manufacture of a medicament for preventing or treating disorders of the CNS.

Items

1. A method for manufacturing an enriched population of microglia cells, the method comprising the steps of:
   a) providing a sample A and optionally a sample B, both comprising bone marrow stromal cells and/or placenta stromal cells and/or umbilical cord stromal cells;
   b) isolating CD11b$^+$, CD45$^-$ microglia progenitor cells from sample A;
   c) i) contacting sample B with a culturing media comprising serum, thereby expanding the bone marrow stromal cells and/or placenta stroma cells and/or umbilical cord stromal cells into mesenchymal stem cells (MSCs); or
      ii) providing MSCs;
   d) contacting the CD11b$^+$, CD45$^-$ microglia progenitor cells of sample A, step (b), with the MSCs of step (c) to generate a sample C;
   e) removing the media comprising serum from sample C;
   f) contacting the serum free sample C of step (e) with a substantially serum free media comprising at least one growth factor; thereby expanding and differentiating the CD11b$^+$, CD45$^-$ microglia progenitor cells;
   g) obtaining an enriched population of microglia cells.
2. An enriched population of microglia cells obtainable by the method according to item 1.
3. An in vitro method for determining the effect of at least one biological agent on a microglia the method comprising:
   a) providing a sample A and optionally a sample B, both comprising bone marrow stromal cells and/or placenta stroma cells and/or umbilical cord stromal cells;
   b) isolating CD11b$^+$, CD45$^-$ microglia progenitor cells from sample A;
   c) i) contacting sample B with a culturing media comprising serum, thereby expanding the bone marrow stromal cells and/or placenta stroma cells and/or umbilical cord stromal cells into mesenchymal stem cells (MSCs); or
      ii) providing MSCs;
   d) contacting the CD11b$^+$, CD45$^-$ microglia progenitor cells of sample A, step (b), with the MSCs of step (c) to generate a sample C; thereby expanding and differentiating the CD11b$^+$, CD45$^-$ microglia progenitor cells;
   e) removing the media comprising serum from sample C;
   f) contacting the serum free sample C of step (e) with a substantially serum free media comprising at least one growth factor;
   g) obtaining an enriched population of microglia cells;
   h) contacting the enriched population of microglia cells with the biological agent; and
   i) determining the effect of the biological agent on microglia.
4. The method according to any one of items 1 and 3, wherein the substantially serum free media further comprises at least one cytokine.
5. The method according to any one of items 1 and 3, wherein the enriched population of microglia cells is in the amount of at least 0.5 million cells, such as at least 1 million cells, for example at least 1.5 million cells, such as at least 2 million cells, for example at least 2.5 million cells, such as at least 3 million cells, for example at least 3.5 million cells, such as at least 4 million cells, for example at least 4.5 million cells, such as at least 5 million cells.

6. The method according to item 3, wherein the biological agent is selected from the group consisting of growth factors, trophic factors, growth factor receptors, neurotransmitters, neuropeptides, neurotrophic factors, hormones, enzymes, cytokines, lymphokines, anti-angiogenic factors, transcription factors, proliferation factors and antibodies.

7. A method for determining genetic risk factors associated with disorders of the CNS and/or psychiatric disorders in a subject, the method comprising:
   a) providing a sample A and optionally a sample B, both comprising bone marrow stromal cells and/or placenta stromal cells and/or umbilical cord stromal cells;
   b) i) isolating CD11b$^+$, CD45$^-$ microglia progenitor cells from sample A;
      or
         i') isolating CD11b$^+$, CD45$^-$ microglia progenitor cells from sample A;
         ii') contacting sample B with a culturing media comprising serum, thereby differentiating the bone marrow stromal cells and/or placenta stroma cells into mesenchymal stem cells (MSCs); or
         iii') providing MSCs;
         iv') contacting the CD11b$^+$, CD45$^-$ microglia progenitor cells of sample A, step (1'), with the MSCs of step (ii') or (iii') to generate a sample C;
         v') removing the media comprising serum from sample C;
         vi') contacting the serum free sample C of step (v') with a substantially serum free media comprising at least one growth factor; thereby expanding and differentiating the CD11b$^+$, CD45$^-$ microglia progenitor cells;
         vii') obtaining an enriched population of microglia cells;
   c) analyzing the gene expression of the isolated microglia progenitor cells or the microglia cells of step (b);
   d) comparing the gene expression of step (c) with the gene expression of a reference cell population; and
   e) determining whether the subject has a gene expression associated with a disorder of the CNS and/or psychiatric disorders.

8. A method for determining biomarkers associated with disorders of the CNS and/or psychiatric disorders, the method comprising:
   a) providing a sample A and optionally a sample B, both comprising bone marrow stromal cells and/or placenta stromal cells;
   b) i) isolating CD11b$^+$, CD45$^-$ microglia progenitor cells from sample A;
      or
         i') isolating CD11b$^+$, CD45$^-$ microglia progenitor cells from sample A;
         ii') contacting sample B with a culturing media comprising serum, thereby differentiating the bone marrow stromal cells and/or placenta stroma cells into mesenchymal stem cells (MSCs); or iii') providing MSCs;

iv') contacting the CD11b$^+$, CD45$^-$ microglia progenitor cells of sample A, step (1'), with the MSCs of step (ii') or (iii') to generate a sample C;

v') removing the media comprising serum from sample C;

vi') contacting the serum free sample C of step (v') with a substantially serum free media comprising at least one growth factor; thereby expanding and differentiating the CD11b$^+$, CD45$^-$ microglia progenitor cells;

vii') obtaining an enriched population of microglia cells;

c) analyzing the gene expression of the isolated microglia progenitor cells or the microglia cells of step (b);

d) comparing the gene expression of step (c) with the gene expression of a reference cell population; and e) determining whether a gene is associated with a disorder of the CNS and/or psychiatric disorder.

9. The method according to any one of items 7 to 8, wherein the reference cell population is a cell population derived from a healthy individual.

10. The method according to any one of items 7 to 8, wherein the gene expression of the reference population has been obtained by said method.

11. The method according to any one of items 7 to 8, wherein the disorder of the CNS is selected from the group consisting of a neurodegenerative disorder, brain tumor and stroke.

12. The method according to item 11, wherein the brain tumor is glioblastoma.

13. The method according to item 12, wherein the neurodegenerative disorder is selected from the group consisting of Alzheimer's disease, Parkinson's disease and multiple sclerosis.

14. The method according to any one of items 7 to 8, wherein the psychiatric disorder is a neurodevelopmental psychiatric disorder.

15. The method according to item 14, wherein the neurodevelopmental psychiatric disorder is selected form the group consisting of nasu-hakola disease, hereditary diffuse leukoencephaly with spheroids, rett syndrome, autism spectrum disorders and obsessive-compulsive disorder.

16. The method according to any one of items 7 to 8, wherein the psychiatric disorder is an adult neuropsychiatric disorder.

17. The method according to item 16, wherein the adult neuropsychiatric disorder is selected from the group consisting of alcohol abuse, drug abuse, depressive disorder, schizophrenia, bipolar disorder, eating disorder and sleep disorder.

18. The method according to any one of items 7 to 8, wherein the reference cell population is a cell population derived from a healthy individual.

19. The method according to any one of items 7 to 8, wherein the gene expression of the reference population has been obtained by said method.

20. An in vitro cell culture of microglia progenitor cells, wherein a) the cells are derived from bone marrow and/or placenta stroma cells and/or /umbilical cord stromal cells;

b) the cell culture is capable of proliferating in a culture medium containing serum;

c) the cells are cultured with mesenchymal stem cells;

d) the cells are CD11b$^+$ and CD45$^-$; and e) the cells in the culture have the capacity to differentiate into microglia in media upon withdrawal of serum and addition of at least one growth factor.

21. The in vitro cell culture according to item 20, wherein the cells are HLA-DR$^-$.

22. The in vitro cell culture according to any one of items 20 to 21, wherein at least 50%, such as 60%, for example at least 70%, preferably at least 80% of the cells are HLA-ABC$^-$.

23. The in vitro cell culture according to any one of items 20 to 22, wherein the media further comprises at least one cytokine.

24. An enriched population of mammalian cells, wherein at least 50%, such as at least 60%, for example at least 70%, preferably at least 80%, more preferably at least 90% of the cells are CD11b$^+$ and CD45$^-$ microglia progenitor cells.

25. The enriched population according to item 24, wherein the enriched population is derived from bone marrow and/or placenta cells.

26. The enriched population according to any one of items 24 to 25, wherein the cells are HLA-DR$^-$.

27. The enriched population according to any one of items 24 to 26, wherein at least 50%, such as at least 60%, for example at least 70%, preferably at least 80% of the enriched population of cells are HLA-ABC$^-$.

28. The cell culture according to any one of items 20 to 23, the enriched population according to any one of items 24 to 27, wherein the microglia progenitor cells express genes selected from the group consisting of TMEM119, MERTK1, GPR34, ENTPD1, CX3CR1, Iba1, P2RY12, GPR34, C1QA, PROS1, CD33, GPR56, CABLES1, BHLHE41, TMEM119, TGFBR1, ENTPD1, ITGB2, ITGAM, AIF, IRF8, ADORA3 and PPARD.

29. The cell culture according to any one of items 20 to 23, the enriched population according to any one of items 24 to 27, wherein the microglia progenitor cells are TMEME119$^+$, CX3CR1$^+$, CD33$^+$, TGFBR1$^+$ and/or ITGAM$^+$.

30. The cell culture according to any one of items 20 to 23, the enriched population according to any one of items 24 to 27, wherein the microglia progenitor cells express transcription factors selected from the group consisting of RUNX1, PU.1 and CSF1R.

31. The cell culture according to any one of items 20 to 23, the enriched population according to any one of items 24 to 27, wherein the cells are CD73$^-$, CD90$^-$ and/or CD105$^-$.

32. The cell culture according to any one of items 20 to 23, the enriched population according to any one of items 24 to 27, wherein the cells do not comprise hematopoietic stem cells.

33. The cell culture according to any one of items 20 to 23, the enriched population according to any one of items 24 to 27, wherein the cells do not comprise mesenchymal stem cells.

34. The cell culture according to any one of items 20 to 23, wherein the culture is capable of at least 6 doublings, such as at least 12 doublings, for example at least 18 doublings.

35. The cell culture according to any one of items 20 to 23, wherein the cells in the culture are mammalian cells.

36. The cell culture according to any one of items 20 to 23, wherein the cells in the culture are human cells.

37. The cell culture according to any one of items 20 to 23, wherein the cells in the culture are murine cells.

38. The method according to any one of items 1, 3 to 8, the cell culture according to any one of items 20 to 23, wherein the growth factor is a neurotrophin or a glial cell line-derived neurotrophic factor (GDNF).

39. The method, the cell culture according to item 38 wherein the neurotrophin is selected from the group consisting of brain-derived neurotrophic factor (BDNF), nerve growth factor (NGF), neurotrophin-3 (NT-3) and neurotrophic 4 (NT-4).

40. The method according to any one of items 1, 3 to 8, the cell culture according to any one of items 20 to 23, wherein the cytokine is selected from the group consisting of M-CSF, IL34, TGF-beta CX3CL1 and CD200.

41. The method according to any one of items 1, 3 to 8, the cell culture according to any one of items 20 to 23, wherein at least some of the cells in culture are capable of differentiating into microglia in the absence of serum from the culture medium.

42. The method according to any one of items 1, 3 to 8, the cell culture according to any one of items 20 to 23, wherein the morphology of the differentiated microglia is semi-ramified or ramified.

43. The method according to any one of items 1, 3 to 8, the cell culture according to any one of items 20 to 23, wherein the cells are phagocytes.

44. The method according to any one of items 1, 3 to 8, the cell culture according to any one of items 20 to 23, wherein the cells are polarized.

45. A method of providing an enriched population of microglia progenitor cells, the method comprising the steps of:
   a. providing a sample A comprising bone marrow stromal cells and/or placenta stromal cells and/or umbilical cord stromal cells;
   b. isolating CD11b$^+$, CD45$^-$, HLA-DR$^-$ microglia progenitor cells from sample A; and
   c. obtaining an enriched population of microglia progenitor cells.

46. The method according to item 45, wherein at least 50%, such as at least 60%, for example at least 70%, preferably at least 80% of the enriched population of microglia progenitor cells are HLA-ABC$^-$.

47. The method according to any one of items 1, 3, 7 to 8 and 45 to 46, the cell culture according to any one of items 20 to 23, the enriched population according to any one of items 24 to 27, wherein the microglia progenitor cells are TMEM119$^+$, MERTK1$^+$, GPR34$^+$, ENTPD1$^+$ and/or CX3CR1$^+$.

48. The method according to any one of items 1, 3, 7 to 8 and 45 to 46, the cell culture according to any one of items 20 to 23, the enriched population according to any one of items 24 to 27, wherein the microglia progenitor cells express Iba1.

49. The method according to any one of items 1, 3, 7 to 8 and 45 to 46, the cell culture according to any one of items 20 to 23, the enriched population according to any one of items 24 to 27, wherein the microglia progenitor cells express transcription factors selected from the group consisting of RUNX1, PU.1 and CSF1R.

50. The method according to any one of items 1, 3, 7 to 8 and 45 to 46, the cell culture according to any one of items 20 to 23, the enriched population according to any one of items 24 to 27, wherein the microglia progenitor cells express genes selected from the group consisting of P2RY12, GPR34, C1 QA, PROS1, CD33, GPR56, CABLES1, BHLHE41, TGFBR1, ENTPD1, ITGB2, ITGAM, AIF, IRF8, ADORA3 and PPARD.

51. The method according to any one of items 1, 3, 7 to 8 and 45 to 46, the cell culture according to any one of items 20 to 23, the enriched population according to any one of items 24 to 27, wherein the microglia progenitor cells express are CD73$^-$, CD90$^-$ and/or CD105$^-$.

52. The method according to any one of items 1, 3, 7 to 8 and 45 to 46, the cell culture according to any one of items 20 to 23, the enriched population according to any one of items 24 to 27, wherein the microglia progenitor cells can differentiate into mature microglia.

53. A composition comprising an enriched population of microglia cells according to any one of items 2 and 24 to 27, and/or a cell culture according to any one of items 20 to 23 and 28 to 37.

54. The composition according to item 53, wherein the composition is a pharmaceutical composition.

55. The composition according to any one of items 53 to 54, wherein the composition further comprises an agent.

56. The composition according to item 55, wherein the agent is an immunotherapeutic agent or a chemotherapeutic agent.

57. An enriched population of microglia cells according to any one of items 2 and 24 to 27, a cell culture according to any one of items 20 to 23 and 28 to 37, or a composition according to any one of items 53 to 56, for use as a medicament.

58. An enriched population of microglia cells according to any one of items 2 and 24 to 27, a cell culture according to any one of items 20 to 23 and 28 to 37, or a composition according to any one of items 53 to 56, for use in the treatment of disorders of the CNS.

59. The enriched population of microglia progenitor cells, the cell culture, or the composition for use according to 58, wherein the disorder of the CNS is selected from the group consisting of glioma, glioblastoma, malignant neoplasm, stroke, Alzheimer's disease, Parkinson's disease and multiple sclerosis.

60. The enriched population of microglia progenitor cells, the culture, or the composition for use according to 58, wherein the disorder of the CNS is a neurodegenerative disorder.

61. The enriched population of microglia progenitor cells, the culture, or the composition for use according to item 60, wherein the neurodegenerative disorder is selected from the group consisting of Alzheimer's disease, Parkinson's disease and multiple sclerosis.

62. The enriched population of microglia progenitor cells, the culture, or the composition for use according to 58, wherein the disorder of the CNS is a psychiatric disorder.

63. The enriched population of microglia progenitor cells, the culture, or the composition for use according to item 62, wherein the psychiatric disorder is a neurodevelopmental psychiatric disorder.

64. The enriched population of microglia progenitor cells, the culture, or the composition for use according to item 63, wherein the neurodevelopmental psychiatric disorder is selected form the group consisting of nasu-hakola disease, hereditary diffuse leukoencephaly with spheroids, rett syndrome, William's Syndrome, autism spectrum disorders and obsessive-compulsive disorder.

65. The enriched population of microglia progenitor cells, the culture, or the composition for use according to item 62, wherein the psychiatric disorder is an adult neuropsychiatric disorder.

66. The enriched population of microglia progenitor cells, the culture, or the composition for use according to item 65, wherein the adult neuropsychiatric disorder is selected from the group consisting of alcohol abuse, drug abuse, depressive disorder, schizophrenia, bipolar disorder, eating disorder and sleep disorder.

67. A method of treating disorders of the CNS in a patient in need thereof, the method comprising administering a therapeutically effective amount of an enriched population of microglia cells according to any one of items 2 and 24 to 27, or a composition according to items 53 to 56.

68. Use of an enriched population of microglia progenitor cells according to any one of items 2 and 24 to 27, or a composition according to any one of items 53 to 56, in the manufacture of a medicament for preventing or treating disorders of the CNS.

EXAMPLES

Example 1. Identification of Microglia-Like Progenitor Cells in the Bone Marrow The stromal compartment of bone marrow was investigated for a microglia-like precursor. Freshly isolated human bone marrow procured from 5 healthy donors (3 females, 2 males of ages between 21 to 35 years old) was analyzed using flow cytometry.

Materials and Methods

A Ficoll gradient centrifugation was performed on bone marrow to procure the mononuclear cell intermediate phase, where mesenchymal stromal cells are also found. Cells were then stained with labelled antibodies binding to the following markers: CD73, CD90, CD105, CD45, CD11b, CD14, CD19, CD34 and HLA-DR.

The following gating strategy was performed for every sample:

Cells were first gated on singlet selection, alive cells and low side scatter to negatively select in first place monocyte/macrophages. Within the remaining fraction, CD14, CD19, CD34 and HLA-DR were used in a first step to discard part of the hematopoietic and endothelial fractions in the bone marrow extractions. Lack of expression of these markers together with CD45 is classically used for the detection of human bone marrow mesenchymal stromal cells (hBM-MSCs). The left stromal fraction was used in a subsequent step for plotting CD11b against CD45 to negatively select the rest of hematopoietic cells.

Results and Conclusion

Results showed that, out of the total cells in the fresh human bone marrow, a 0.04±0.01% is HLA-DR⁻/CD14⁻/CD19⁻/CD34⁻/CD45⁻/CD11b⁺ (FIG. 1). This population is referred to as the stroma microglia progenitor (STR-MP). A 97.9±1.1% of TRM-progenitor cells were negative for CD73, a 99.8±0.1% were negative for CD90, and 97.7±1.1% were negative for CD105 (FIG. 1).

Example 2. Genetic Analysis of the Isolated Microglia-Like Progenitor Cells

The non-hematopoietic CD11b$^+$ cell detected in the stroma compartment were sorted for a single cell analysis on their genetic expression pattern based on a battery of genes reported to be specifically expressed in microglia progenitors, microglial development and central nervous system pathogenesis associated to specific microglial genes.

Materials and Methods

Genes were analyzed by means of fluidigm. Lysis buffer was added to 48 well plates. One CD11b$^+$ cells was then sorted in each well according to the gating strategy provided in Example 1. Cells were then prepared for fluidigm processing for 48 selected genes according to the manufacturer's instructions. The gene expression was read according to the manufacturer instructions.

Results and Conclusion

Results confirmed that the sorted cells express the typical microglial progenitor gene panel (Table 1). They expressed microglia myeloid-associated RUNX1, PU.1 and CSF1 R transcription factors, which are essential genes for regulation of microglia cell development (Ginhoux et al. 2010, Kierdorf et al. 2013), and include the expression of P2RY12, GPR34, C1QA, and PROS1, that have been reported for being expressed in human adult microglia but not in human blood-derived monocytes (Butovsky et al. 2014). Other canonical microglial genes expressed also included CD33, GPR56, CABLES1, BHLHE41, TMEM119, TGFBR1, ENTPD1, ITGB2, ITGAM, AIF, IRF8, ADORA3 and PPARD (Kierdorf et al. 2013, Butovsky et al. 2014, Muffat et al. 2016, Zhang et al, 2014, Pandya et al. 2017, Hickman et al. 2013). The posterior unbiased whole-transcriptome analysis indicated that this myeloid progenitor population may include different myeloid cell types whose gene expression profiles can exclude Myb and Batf3, and together with the exclusion of CD34 marker when sorting, can indicate the presence in the bone marrow of a Myb-independent yolk sac erythromyeloid progenitor similar to what has been described for microglia Kierdorf et al. 2013, Butovsky et al. 2014, Muffat et al. 2016, Zhang et al, 2014, Pandya et al. 2017, Hickman et al. 2013, Schulz et al. 2012).

TABLE 1

| Stroma microglia gene expression. | |
|---|---|
| Genes | Expressed |
| IRF8 | X |
| PU.1 | X |
| RUNX1 | X |
| MYB | X |
| IRF4 | X |
| ID2 | X |
| BATF3 | X |
| KLF4 | X |
| TMEM119 | X |
| MERTK1 | X |
| PPARD | X |
| OLFML3 | X |
| ITGAM | X |
| ITGB2 | X |
| CSF1R | X |
| ADORA3 | X |
| AIF1 | X |

TABLE 1-continued

Stroma microglia gene expression.

| Genes | Expressed |
|-------|-----------|
| GPR56 | X |
| BIN1 | X |
| APOE | X |
| TREM2 | X |
| ENTPD1 | X |
| TGFB1 | X |
| TGFBR1 | X |
| P2RY12 | X |
| C1QA | X |
| PROS1 | X |
| GAS6 | X |
| CABLES1 | X |
| BHLHE41 | X |
| SLCO2B | |
| SLC7A8 | X |
| CD33 | X |
| HEXB | X |
| DRD4 | X |
| SLC6A3 | |
| CACNA2C | |
| MTHFR | X |

Example 3. Characterization of the Isolated Microglia-Like Progenitor Cells

Stromal cultures were tested for the retention upon early and late passages of specific microglial surface markers like CD11b and CX3CR1, and included the microglia markers for Iba1, TMEM119 and HLA-DR.

Materials and Methods

Glass coverslips were pre-treated with laminin and poly-ornitine. Isolated stromal cells (Example 1) were seeded on pre-treated coverslips (previously introduced in 24 multi well plates). The cells were allowed to survive in the medium of interest. Functional analysis were performed or cells were fixed with cold paraformaldehyde 4% (4% PFA) followed by staining for immunocytochemistry with the surface markers listed below. Marker combinations tested:

1) Iba1$^+$ and CD11b$^+$
2) Iba1$^+$ and TMEM119$^+$
3) TMEM119$^+$ and HLA DR$^-$
4) Iba1$^+$ and CX3CR1$^+$
5) TMEM119$^+$ and CD33$^+$

Results

Half of the fresh bone marrow sample from 2 healthy donors (1 male and 1 female of 21 and 24 years old, respectively) was frozen and kept at −150° C. until their further use, whilst the other half was put in contact with plastic and expanded for a lentiviral infection at passage 4 to express the green fluorescence protein (GFP). The infected hBM-MSCs were subjected to a posterior selection of 5 days based on puromycin to select the GFP$^+$ hBM-MSCs. After this GFP$^+$ hBM-MSCs selection, the fresh bone marrow stromal cell sample that was kept at −150° C. was used as previously described in the example 1 for isolating the human stroma microglia. The isolated cells were isolated and put in culture with their correspondent GFP$^+$ hBM-MSC halves. Cells were allowed to recover for 48 h in the expansion serum-containing medium that we refer to as basal medium (BM). After these 2 days, the medium was changed to a serum free medium supplemented with a combination of growth factors (GF) for 9 days. Cell morphology of the STR-MP 12 h after sorting resembled a cubic cell in prophase (FIG. 2Ba, 2Ba'). Sorted cells can be found in close interaction with their feeder hBM-MSC layer (FIG. 2Bb). After 2 days, the medium was changed from a serum-containing medium to a serum-free condition supplemented with GF aiming at the STR-MP to show ramifications (FIG. 2Bc, 2Bd). After 9 days, cells were dying and the experiment was terminated for a posterior Iba1 and TMEM119 immunocharacterization, since according to the single cell gene analysis, these 2 markers should be expressed on this type of cell (Table 1).

Figure 3:
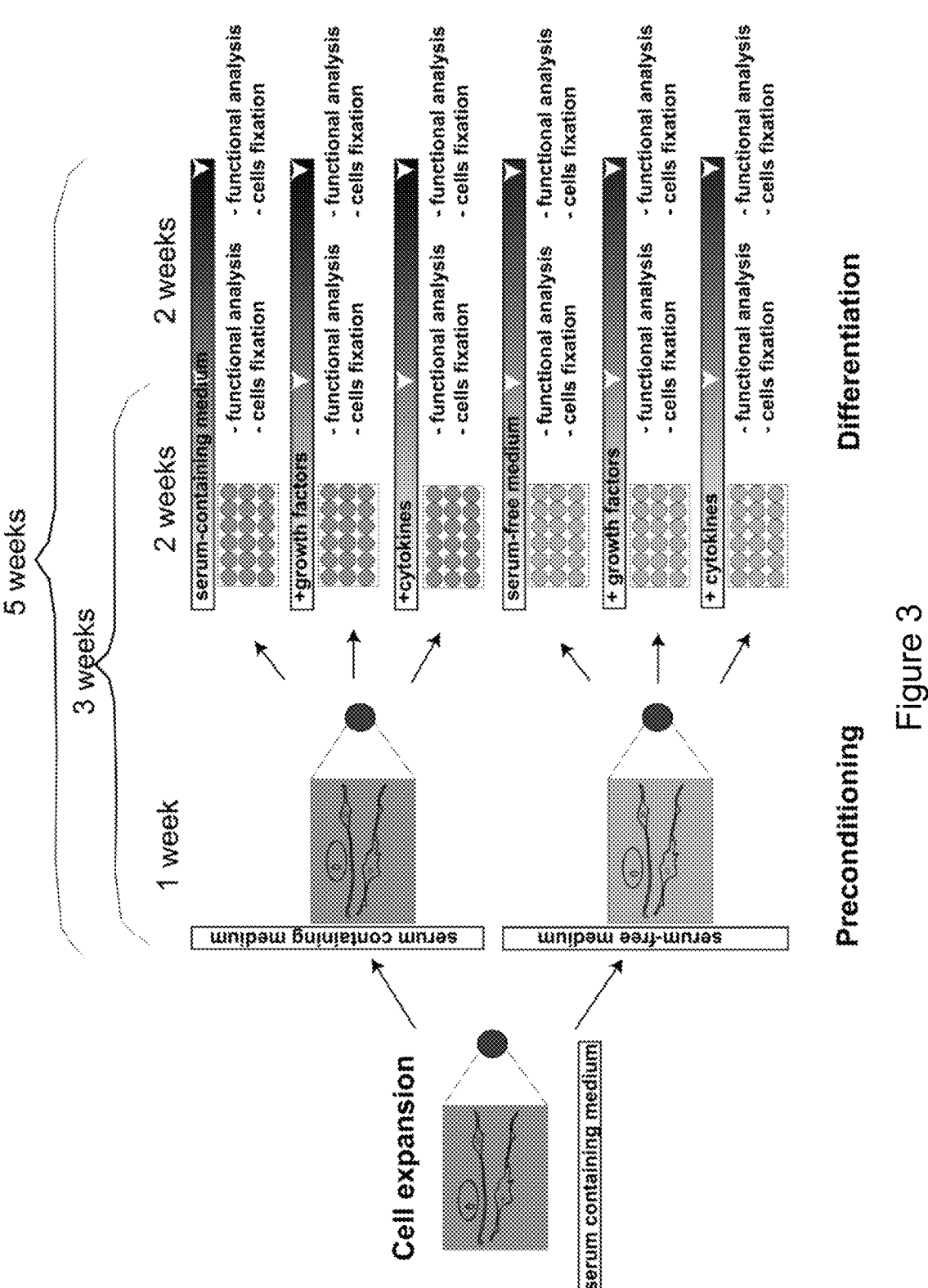
FIG. 3. A. Scheme depicting the experimental design of the in vitro work. After a first week of acclimation to the serum-free media in flasks, cells are seeded on polyornithine and laminin coated coverslips. Cells are then exposed to the NT or CK for 2 or 4 weeks, making short- and long-term time points of 3- and 5-weeks total. At these time points, cells can be subjected to functional analysis and/or be fixed with paraformaldehyde 4% (4% PFA) for a posterior immuno- and morphological analysis. This analysis was done using Cellomics high content screening, as described in the section for Analysis under Material and Methods.

Identification of Serum-Containing and Serum-Free Conditions for Stroma Microglia Culture serum-containing expansion medium or basal medium (BM) was supplemented with a cocktail of a) BDNF and NT3 or b) IL-34, M-CSF and TGF-β, that we will refer to as growth factors (GF) or cytokines (CK) conditions, A serum-free medium condition was included to closely mimic the intact CNS environment and to determine possible effects of serum, as previously studied for murine microglia cell models (Bohlen et al. 2017) (FIG. 3). 3 and 5 week time-points were included after which cells were fixated for posterior immunocytochemistry studies for well accepted markers for microglia/myeloid cells such as Iba1 and CD11b; Iba1 and TMEM119; TMEM119 and HLA DR; TMEM119 and CD33 and Iba1 and CX3CR1. All the analysis quantification was done using Cellomics high content screening.

Figure 2:
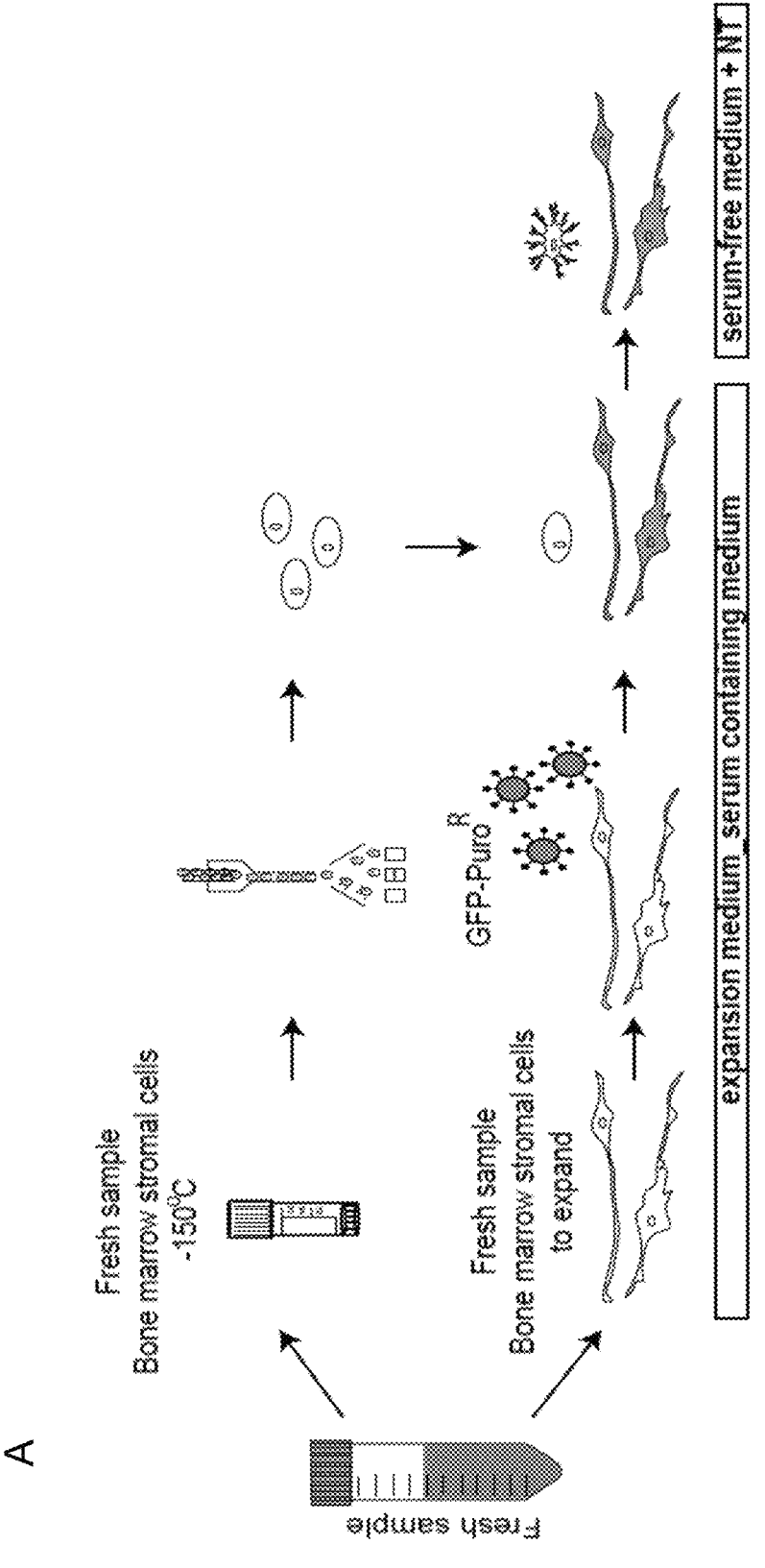
FIG. 2. Non-hematopoietic CD11b$^+$ cells grow as part of the mesenchymal stromal cultures, that act as a feeder cell layer. A. Scheme depicting the experimental design for studying the non-hematopoietic CD11b$^+$ cells' morphology and culture needs. B.a. Twelve hours after sorting, sorted cells were found on plastic and in close contact with GFP$^+$ hBM-MSCs. Sorted cells showed a cubic cellular shape (denoted by an asterisk, scale bar: 20 m; magnification in the upper frame to the right, a'. Scale bar: 10 μm). B.b. In order to force a morphological change, cells were exposed to a serum-free medium supplemented with neurotrophins (NT) to promote survival of hBM-MSC. B. c, d. After 2 days of serum-free conditions different ramified morphologies could be observed (asterisk). Cells were able to survive for 5 days in plastic and in contact with stromal cells (B. d). C. The CD11b$^+$ Iba1$^+$ small cells could be tracked in the hBM-MSCs cultures attending to the nuclear size of the cells and to their immunoreactivity to Iba1. D. Analyzed by means of the software ThermoScientific HCS Studio: Cellomics Scan, we next analyzed the compartment for small nuclei sub-group, a difference was observed between the two studied time points of 3 and 5 weeks. The compartment for small nuclei co-expressing Iba1 and CD11b was found to significantly increase in numbers under the BM+CK condition. E. The expression of classic microglia markers Iba1, TMEM119 and CX3CR1 were included to determine if cells keep their expression under the different culturing conditions and HLA-DR was included to confirm the absence of it. BM: basal medium, a.k.a. expansion medium. BM+NT: basal medium supplemented with neurotrophins. BM+CK: basal medium supplemented with cytokines.

Results showed the presence of distinct populations defined by the combination of Iba1 expression and the cells' nuclei area. This Iba1$^h$CD11b$^h$ small cells group displayed an ameboid compressed cytoplasm, as expected from the previous sorting studies. According to the Cellomics analysis, the Iba1$^h$CD11b$^h$ cells' nuclei area is restricted to 100 to 400 pixels$^2$, this corresponding to 40 to 156 μm$^2$. For subsequent analysis on small cells proportions, the cell nucleus size of up to 400 pixels$^2$ (156 μm$^2$) was restricted and combined with the above-mentioned markers. The data did not show any significant differences in the overall proportions between any studied condition or any given time point (FIG. 2). Nevertheless, and within the group of small cells, an increased proportion of Iba1$^+$ CD11b$^h$ cells was seen at 5 weeks under the BM+CK condition (FIG. 2). hBM-MSCs and Iba1$^h$CD11b$^h$ small cells did not survive well under any serum-free medium condition, even if supplemented with GF or CK.

Figure 4:
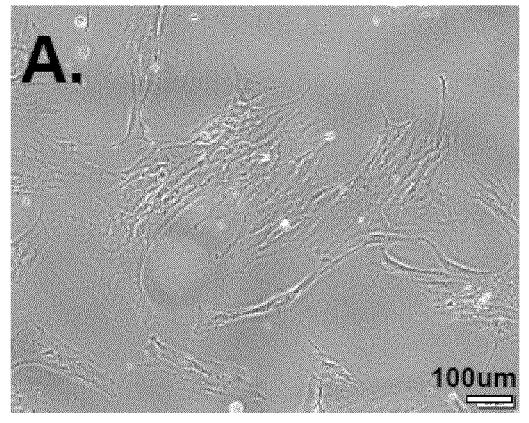
FIG. 4. Characterization of aging non-hematopoietic CD11b$^+$ cells. A. Representative case showing the morphology of the human stromal cells, containing hBM-MSCs and the non-hematopoietic CD11b$^+$ cells, before cells start to age. Scale bar 100 m. B. Representative case of a hBM-MSCs bearing the non-hematopoietic CD11b$^+$ cells culture that denotes the change in morphology when cells age upon passages. Scale bar 50 m. C. Non-hematopoietic CD11b$^+$ cells were detected based on their CD11b and Iba1 co-expression. D. The graph shows the % of cells in aging cell cultures expressing the classic microglia markers Iba1, TMEM119 and CX3CR1 across the culturing serum-containing conditions. E. The graph shows the % of cells in aging cell cultures under serum-free conditions for the classic microglia markers Iba1, TMEM119 and CX3CR1. F. Graph showing the % of the ameboid morphology amongst serum free conditions. G. Graph showing the % of the semi-ramified morphology amongst serum free conditions. H. Graph showing the % of the ramified morphology amongst serum free conditions. NM: neuronal medium, a.k.a. expansion medium. NM+NT: neuronal medium supplemented with neurotrophins. NM+CK: neuronal medium supplemented with cytokines.
Figure 4:
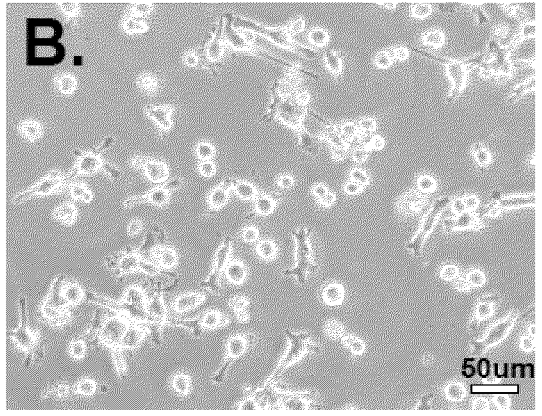
Figure 4:
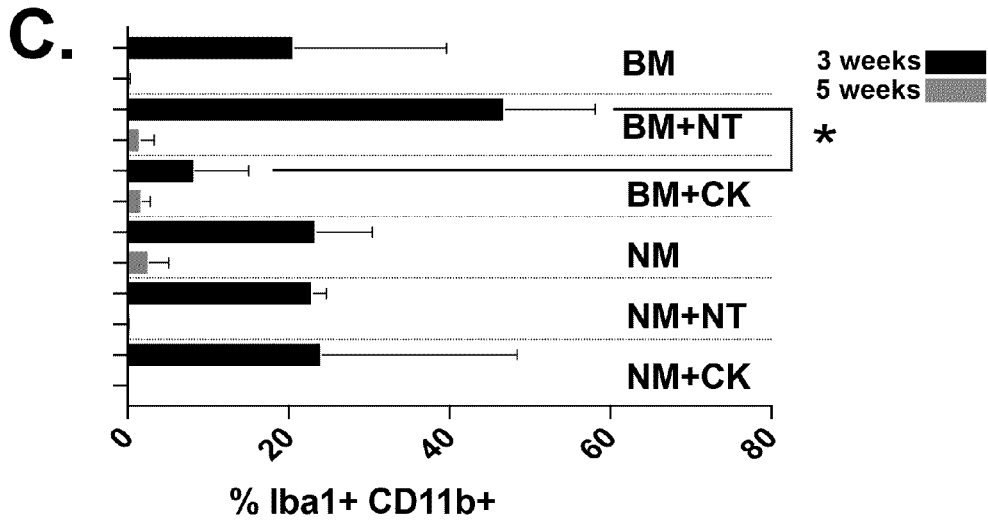

Identification of Serum-Containing and Serum-Free Conditions for Aging Stroma Microglia Culture The influence of in vitro aging on cellular characteristics for stem cell based therapies is important to consider (Yang et al. 2018). The effect of the different culturing media on aging hBM-MSCs and stroma microglia defined by its content on CD11b and Iba1 was assessed by expanding the cells until an apparent morphological change due to aging could be observed (FIGS. 4A and 4B). Under this condition, small Iba1$^+$ CD11b$^h$ cells were considered to be stroma microglia, the cells of interest. Aging Iba1$^+$ CD11b$^h$ cells tended to disappear at the 5 week time point in all conditions (FIG. 4C). Aging cells expressed TMEM119 and CX3CR1 but did not express HLA-DR (FIG. 4D). Of note is that aging Iba1$^+$ CD11b$^h$ cells could survive under serum-free condition (FIGS. 4C and 4E) and expressed TMEM119, CX3CR1 and a few cells were positive for CD33 under serum containing and serum-free conditions at 3 weeks.

Classical microglia morphologies appear under serum free conditions in aging cell cultures. Cells were classified under 3 main morphological types: 1) ameboid or round-shaped, which could indicate an activated state of the cell; 2) semi-ramified, when the cell showed one extension sprouting from its soma and 3) ramified, when the cell showed more than one extension sprouting from its soma. An unbiased manual analysis was performed to determine morphologies under the different serum-free conditions. The analysis showed that the serum-free condition supplemented with GF promotes semi-ramified and ramified morphologies on Iba1$^+$ CD11b$^h$ cells, whilst CK serum-free promotes ameboid cell morphologies.

Conclusion

The derivatives of the STR-MP in vitro, which we will be referring to as stroma microglia (STR-M), retained the expression of microglia specific markers upon passaging. Moreover, the use of cytokines in a serum-containing medium (M-CSF, IL34 and TGF-beta) could increase the numbers of the CD11b population (STR-MP) at early passages whilst neurotrophines in a serum-containing medium (BDNF and NT3) impacted their numbers at late passages (aging cultures).

Example 4. Stroma Microglia Presents Phagocytic and Immune-Polarization Abilities Stromal cultures were tested for their ability to phagocyte and polarize upon lipopolysaccharide (LPS) activation at early and late passages, aka non-aging and aging cultures.

A possible culturing conditions' impact on the cell's functions was also studied, as the presence of serum or growth factors in the medium can impact the phagocytic ability. Although stroma microglia phagocyte in not aging and aging condition the effect of the different culturing conditions can have an impact. Phagocytic ability measured as the ratio of GFP$^+$ latex beads phagocyted by the Iba1$^+$ CD11b$^+$ stroma microglia appears with time and under the presence of serum and/or cytokines in young cultures and becomes different in aging Iba1$^+$ CD11b$^h$ cells. The number of phagocytic Iba1$^+$ CD11b$^h$ stroma microglia cell does not depend on the medium condition.

To determine if stroma microglia can be "classically activated" and to address whether different culture conditions might impact LPS activation as might impact maturational processes, cultures were exposed to LPS under serum-free culturing conditions.

Materials and Methods

Microglial Phagocytosis Assay

Fluorescence latex beads of 1 um diameter were first preopsonized for 1 h at 37° C. at a ratio of 1:5 with fetal bovine serum. Preopsinized beads were subsequently diluted in the different serum-containing and serum free culture conditions for a final concentration of latex beads of 0.01%. Cells were in contact with medium and preopsonized latex beads for 1 h at 37° C. and subsequently fixed with cold 4% PFA solution for a posterior immunohistochemistry study for CD11b and Iba1 expression.

Lipopolysacharide Induced Activation

Cell cultures were incubated overnight (O/N) with 100 ng/ml of lypopolycacharide (LPS) added to the different serum-containing and serum free culture conditions. After O/N incubation, supernatants were collected for an ELISA against TNF-α, a proinflammatory cytokine that is reported not to be secreted by BM-MSCs but by microglia, and cells were fixed in 4% PFA solution for cluster differentiation 40 (CD40) study, a human marker for M1 activation, and CD11b.

Results and Conclusion

Figure 5:
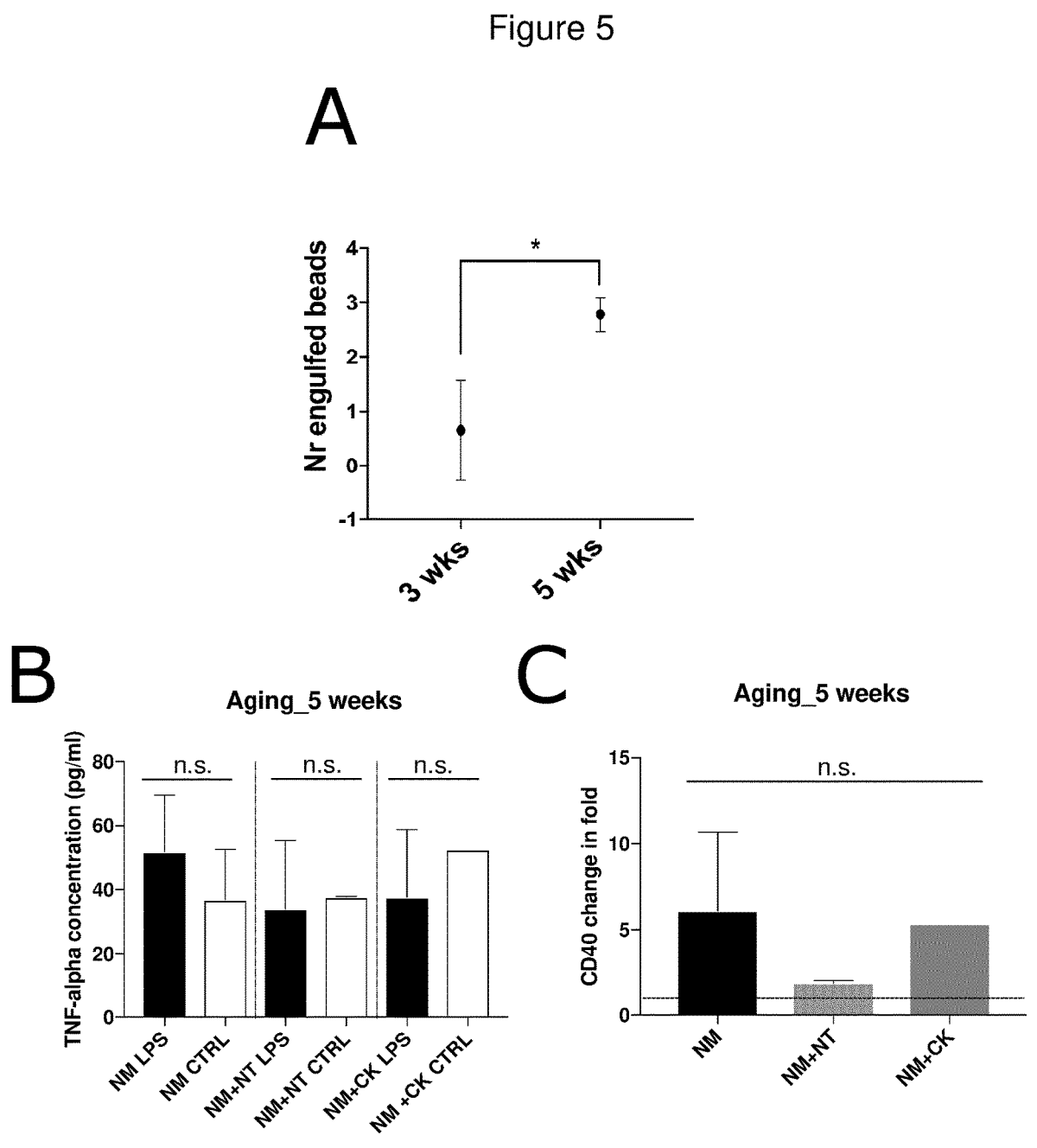

Stroma microglia shows phagocytic and polarization abilities. The phagocytic ability can be increased on aging cultures by exposing to a serum containing medium supplemented with CK. In addition, TNF-α is secreted to the medium and can be detected in the supernatants. Upon LPS, stroma microglia showed an increased intensity for the immunoreactivity towards CD40, clearly indicating a proinflammatory activation (FIG. 5).

Example 5. Stroma Microglia Retains the Capability to Survive in an Ex Vivo Human Brain Organotypic Model In order to address survival and integration properties in the central nervous system (CNS), the ability of stroma microglia to survive in an ex vivo human glioblastoma tissue was investigated.

Human brain tissue from brain tumor resections was sliced for organotypic culturing and received the grafting of GFP$^+$ stroma microglia as part of the GFP$^+$ hBM-MSCs population.

Materials and Methods

Ex Vivo Experiments

The surgically resected adult human cortical tissue (hACtx) was immediately kept in ice-cold artificial cerebrospinal fluid and then transferred to a slicing chamber of a Vibratome filled with ice-cold dissection medium. Slices were transferred to 24-well plates containing ice-cold dissection medium with one slice per well. The slices were then transferred to Millicell cell culture inserts in six-well plates containing 1:1 ratio of dissection medium and slice culture medium (Neurobasal medium, 2% B27 without vitamin A, 0.5% N2, 0.5 mM L-glutamine, 0.1% human albumin with 100 U/mL penicillin/streptomycin) and incubated in 5% CO2 at 37° C. Twenty-four hours later the medium was completely changed to slice culture medium, which was changed once a week. The slices were checked for their viability by fixing the slice in 4% PFA and they were then assessed by immunocytochemistry for neuronal (MAP2, FOX3, and SMI 311) and glial (GFAP) markers. Non-transduced hACtx slice cultures were used for co-cultures with iCtx cells. The miR124.T-GFP reporter and SynI-RFP transduced 10 dpi HEFL and iCtx cells (BMF combination) were transplanted on top of the slices at 2 weeks after the start of culturing and then co-cultured for another 3 weeks before they were fixed in 4% PFA and assessed by immunocytochemistry. hACtx slices were washed with slice culture medium at least twice before co-culture with iCtx cells. At the end of additional 2 weeks in culture, slices fixed in ice cold 4% PFA and stained.

Results and Conclusion

The stroma microglia have the capability to survive in an ex vivo human brain organotypic model. In addition, it shows to retain the expression of the specific markers for microglia after their engraftment in the human CNS, such as expression of CD11b and, importantly, TMEM119. In addition, the observed morphology of the surviving stroma microglia indicates that these cells can integrate (they can extend ramifications) and polarize.

Example 6—Stroma Microglia Cells are HLA DR⁻ and HLA ABC⁻

The stromal compartment of bone marrow was investigated for the expression of HLA-ABC in the microglia-like precursor cells that are selected based on the absence of HLA-DR expression (as described in Example 1). The stroma microglia progenitor cells are by definition HLA-DR⁻. Freshly isolated human bone marrow procured from 5 healthy donors (3 females, 2 males of ages between 21 to 35 years) was analyzed using flow cytometry as follows.

Materials and Methods

A Ficoll gradient centrifugation was performed on bone marrow to procure the mononuclear cell intermediate phase, where mesenchymal stromal cells are also found. Cells were then stained with labelled antibodies binding to the following markers: HLA-ABC, CD45, CD11b, CD14, CD19, CD34 and HLA-DR.

The following gating strategy was performed for every sample:

Cells were first gated on singlet selection, alive cells and low side scatter to negatively select in first place monocyte/macrophages. Within the remaining fraction, CD14, CD19, CD34 and HLA-DR were used in a first step to discard part of the hematopoietic and endothelial fractions in the bone marrow extractions, i.e. cells negative for these markers were selected. Lack of expression of these markers together with CD45 is classically used for the detection of human bone marrow mesenchymal stromal cells (hBM-MSCs). The left stromal fraction was used in a subsequent step for plotting CD11b against CD45 to negatively select the rest of hematopoietic cells. From this compartment, cells were studied on the expression of HLA-ABC.

Results and Conclusion

Figure 6:
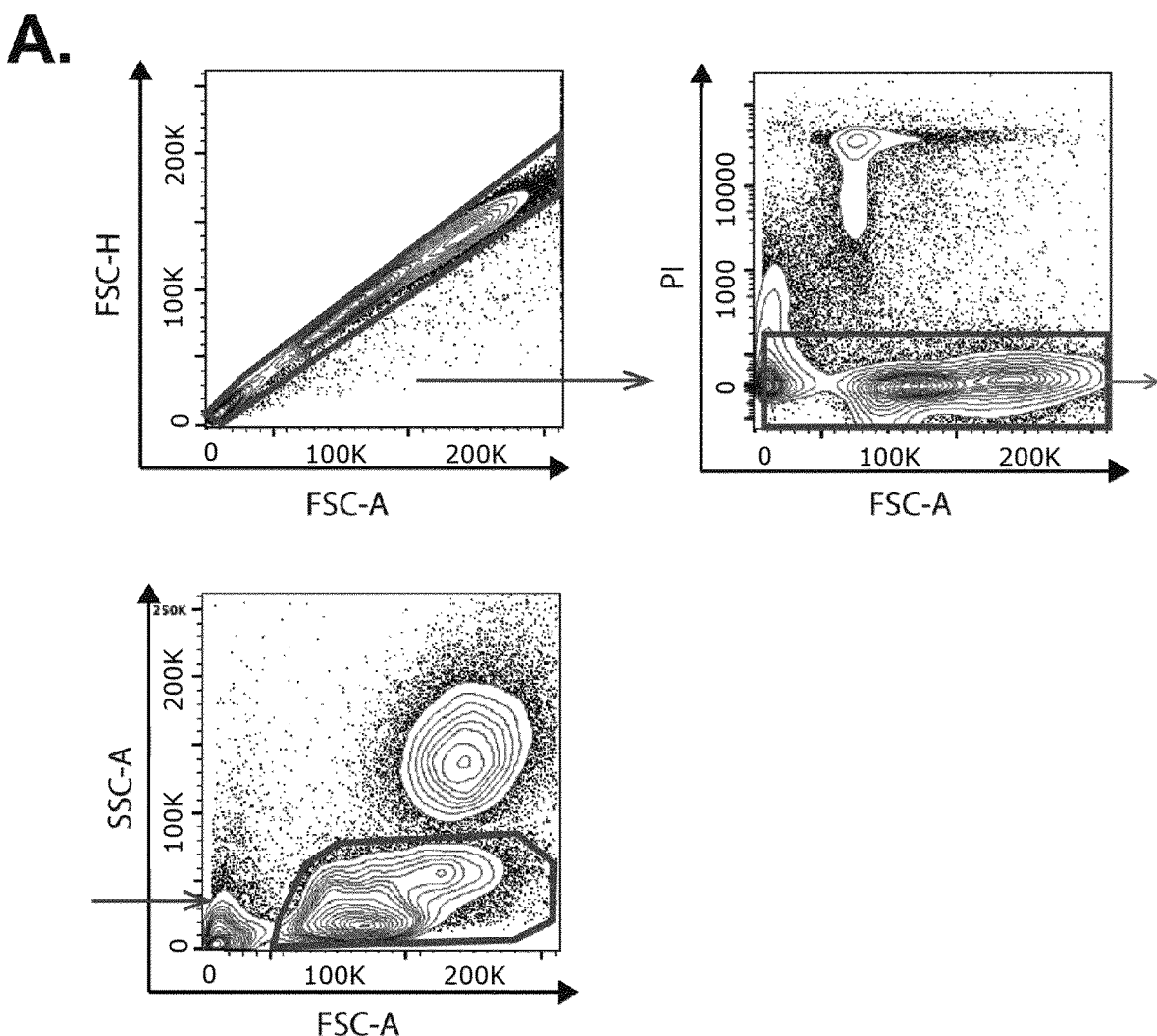
FIG. 6. Human bone marrow stromal cells harbor non-hematopoietic CD11b$^+$ cells that express microglial-specific genes. A.-F. Representative case showing the gating strategy for detecting non-hematopoietic CD11b$^+$ cells. Cells negative for markers HLA-DR/CD14/CD19/CD34 that label endothelial and hematopoietic lineages and hematopoietic stem cells were selected within the compartment of living cells. Selected cells (HLA-DR$^-$/CD14$^-$/CD19$^-$/CD34$^-$/CD45$^-$/CD11b$^+$) were analyzed for HLA-ABC mesenchymal markers (n=5 donors). Within the HLA-DR$^-$/CD14$^-$/CD19$^-$/CD34$^-$/CD45$^-$/CD11b$^+$ compartment, most cells were HLA-ABC$^-$ (82.7±9.2%).
Figure 6:
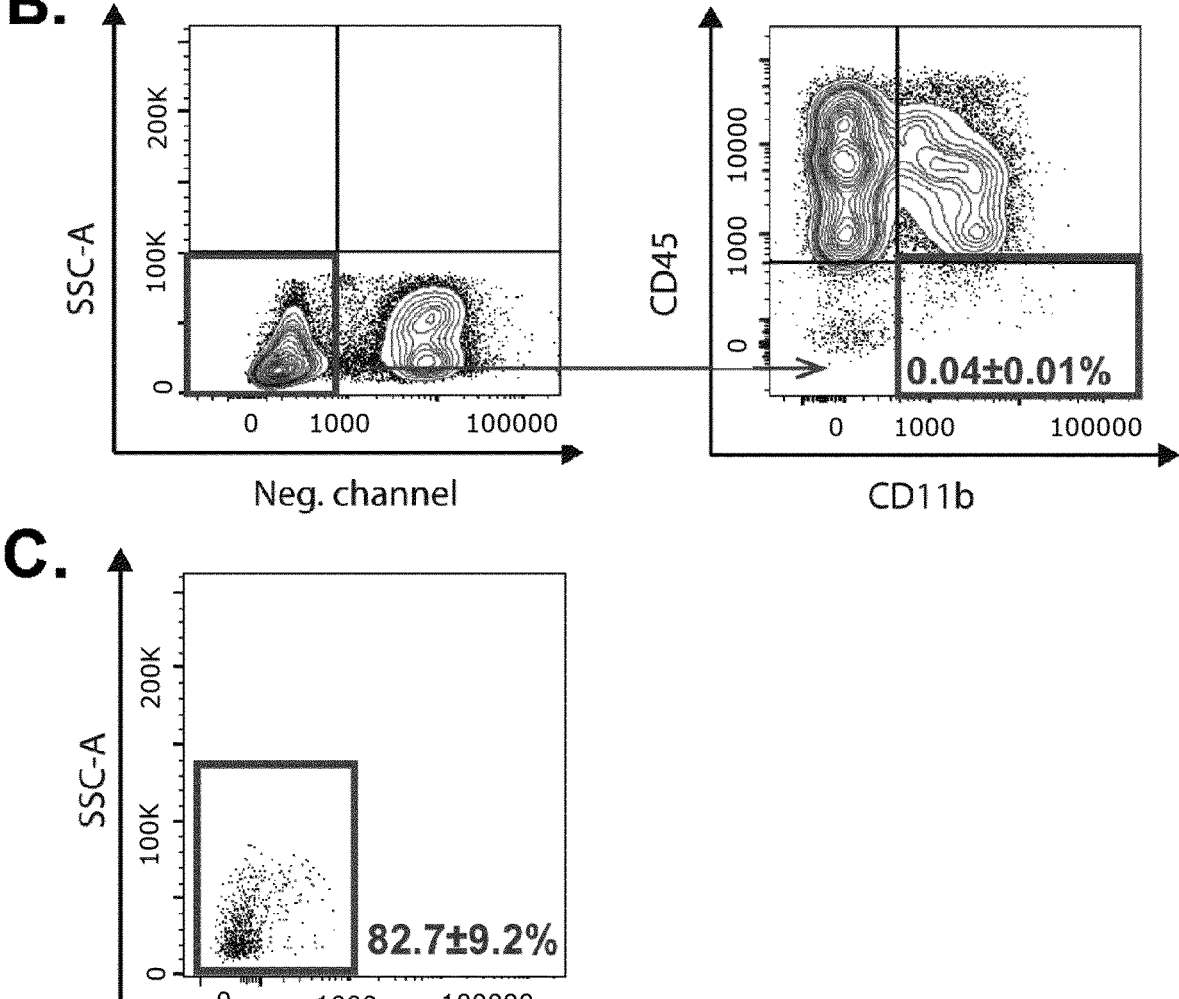

The results showed that, out of the selected 0.04±0.01% of the cells which is the HLA-DR⁻/CD14⁻/CD19⁻/CD34⁻/CD45⁻/CD11b⁺ compartment (FIG. 6A, B), 82.7±9.2% of the STR-MP cells were negative for HLA-ABC (FIG. 6C), demonstrating that the stroma microglia progenitor compartment is 1) negative to HLA-DR by definition and 2) preferentially negative for HLA-ABC.

Example 7—Stroma Microglia Cells do not Secrete TNF-α after LPS Stimulation

In order to address the ability of stroma microglia cells to secrete the TNF-α proinflammatory cytokine when exposed to lipopolysaccharide (LPS) treatment for polarizing the cells, stroma microglia progenitors (STR-MP) were isolated from 4 different human donors (as in Examples 1 and 6), and put to differentiate for 5 days in neuronal medium (medium with no serum) alone or supplemented with a cocktail of a) BDNF and NT3 or b) IL-34, M-CSF and TGF-β. These conditions will be referred to as growth factors (GF) or cytokines (CK) conditions.

Material and methods: FACS sorted stroma microglia progenitors (as described in Example 1 and 6) were seeded and allowed to recover from sorting for 24 h. Next day, cells were subjected to a pre-differentiation protocol towards the stroma microglia progenitor cell derivative christened as stroma microglia cells, Stroma microglia cell cultures were incubated overnight (O/N) with 100 ng/ml of lipopolysaccharide (LPS) added to the different serum free culture conditions, specifically neuronal medium (medium with no serum) alone or supplemented with a cocktail of a) BDNF and NT3 or b) IL-34, M-CSF and TGF-β, supernatants were collected for an ELISA against TNF-α.

Results and Conclusion

Figure 7:
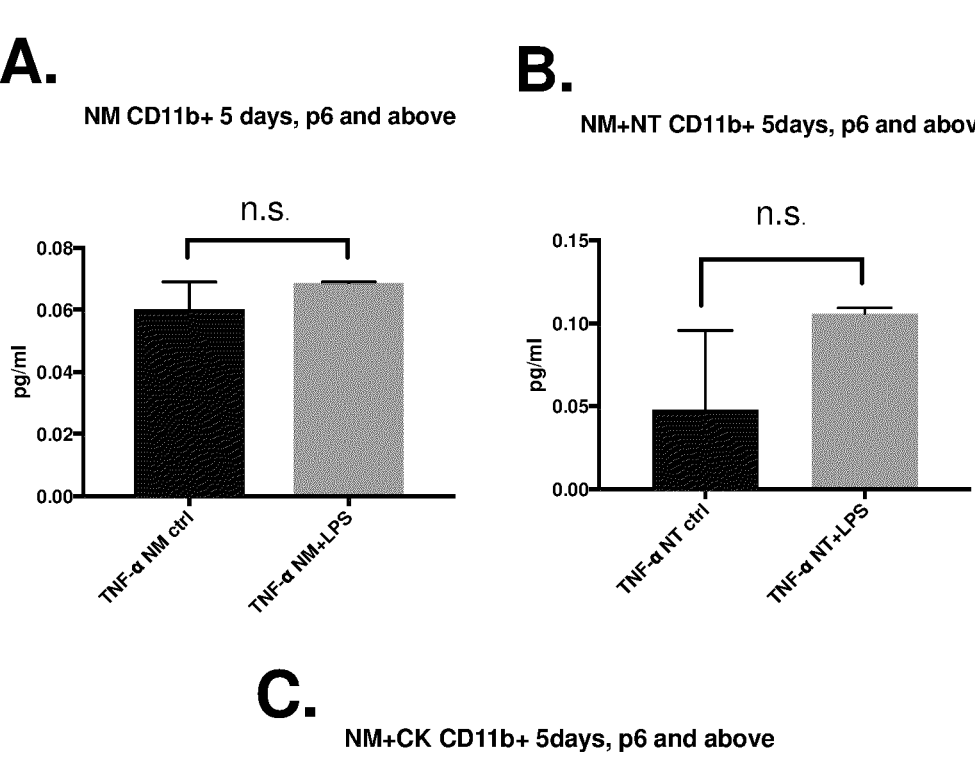
FIG. 7. Classical activation of stroma microglia (STR-M) after 5 days of exposure to (A) neuronal medium (NM, serum free conditions), (B) NM supplemented with growth factors (NT) and (C) NM supplemented with cytokines (CK). No significant difference in the levels of the proinflammatory cytokine TNF-α was detected in the supernatant by means of ELISA upon 24 h exposed to LPS (n=3 donors; paired, one-tailed Student-T test. p≥0.05).
Figure 7:
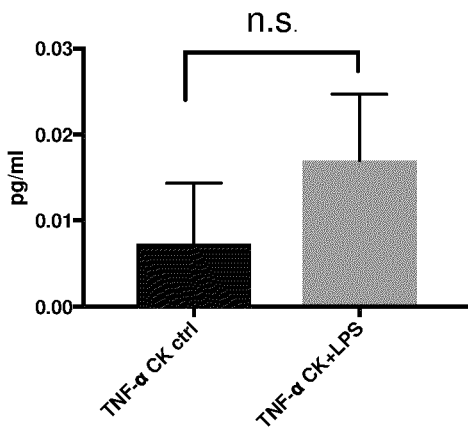

Classical activation of stroma microglia (STR-M) after 5 days of exposure to neuronal medium (NM, serum free conditions) (FIG. 7a), NM supplemented with growth factors (NT) (FIG. 7b) and NM supplemented with cytokines (CK) (FIG. 7c). No significant difference in the levels of the proinflammatory cytokine TNF-α was detected in the supernatant by means of ELISA upon 24 h exposure to LPS (n=3 donors; paired, one-tailed Student-T test, p; 0.05). Our results show that, although STR-M cells can polarize and become activated (Examples 3 and 8), they do not secret TNF-α.

Example 8—the Present Disclosure Provides a Rapid Method of Providing Microglia-Like Cells In order to investigate how fast the stroma microglia progenitors (STR-MP) can derive a more mature and functional derivative cell type (stroma microglia or STR-M), STR-MP were isolated, as described in Examples 1 and 6, and, after seeding and recovering for 24 h, exposed to pre-differentiating conditions. Different conditions were used; serum-free or supplemented with growth factors (GF) or cytokines (CK) (as in Examples 3 and 7). STR-M cells were tested for its functionality as a mature cell and studied for the expression of the galactin3 and Iba1 microglia markers.

Material and methods: FACS sorted stroma microglia progenitors (as described in Examples 1 and 6) were seeded and allowed to recover from sorting for 24 h. Next day, cells were subjected to a pre-differentiation protocol towards the stroma microglia progenitor cell derivative christened as stroma microglia cells. Stroma microglia cell cultures were incubated overnight (O/N) with 100 ng/ml of lipopolysaccharide (LPS) in the serum-free culture conditions, particularly neuronal medium (medium with no serum) only or supplemented with a cocktail of a) BDNF and NT3 or b) IL-34, M-CSF and TGF-ß, i.e. the GF and CK conditions. After O/N incubation, supernatants were collected for measurement of the release of a number of proinflammatory cytokines using MesoScale (MSD) plates with the proinflammatory panels for IFN-γ, IL-1β, IL-2, IL-4, IL-5, IL-6, IL-8, IL-10, IL-12 and TNF-α. After supernatant collection, the cells were fixed with the fixative paraformaldehyde 4% and immunostained for the microglia markers Iba1 and galactin3.

Results and Conclusion

Figure 8:
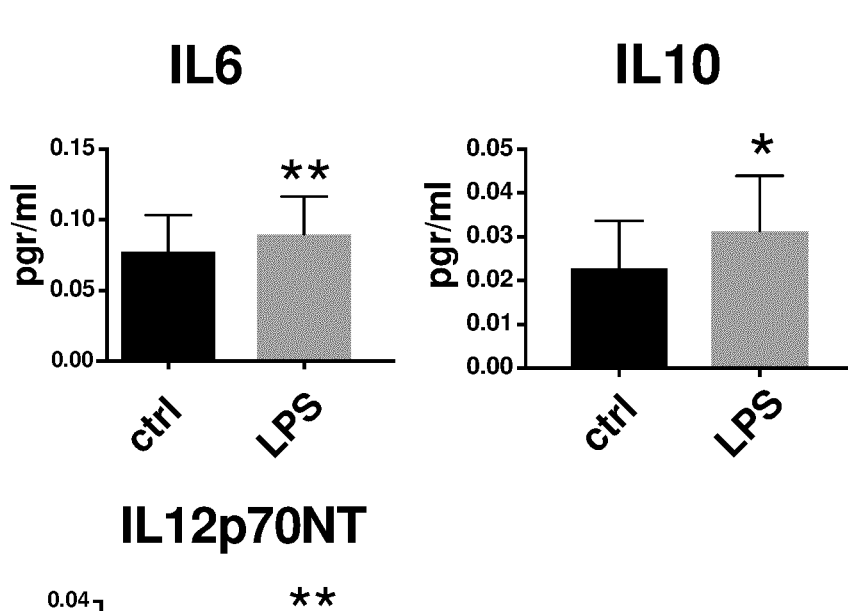
FIG. 8. Cytokine secretion upon LPS activation and immunocytochemical characterization of stroma microglia (STR-M) CD11b$^+$ cells. A. Classical activation of STR-M after 5 days of exposure to NT in serum free conditions. An increased secretion of the proinflammatory cytokines secretion of IL6, IL 10 and IL12p70NT were detected upon 24 h exposed to LPS (n=3 donors; paired, one-tailed Student-T test, *p<0.05; **p<0.01). B. Classical activation of STR-M after 5 days of exposure to CK in serum free conditions. An increased secretion of the proinflammatory cytokines secretion of IL4, IL6, IL10 and IL13 was detected (n=3 donors; paired, one-tailed Student-T test, *p<0.05; **p<0.01). C. STR-M cells, defined to be the derivative cells of the stroma microglia progenitors (STR-MP) FACS-sorted HLA-DR$^-$/CD14$^-$/CD19$^-$/CD34$^-$/CD45$^-$/CD11b$^+$ cells after 5 days of exposure to serum free conditions, express the known microglia markers Iba1 (left) and Galectin-3 (right). Nuclei are stained with DAPI. Scale bar: 20 um.
Figure 8:
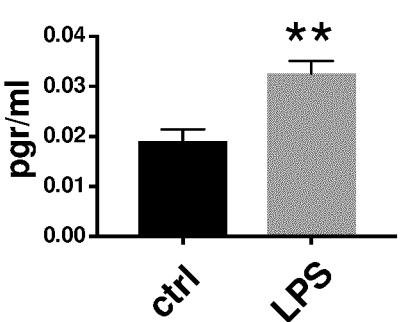

Our results show that, after being exposed to NT (NM supplemented with growth factors) and CK conditions for only 5 days, STR-M can be classically activated (FIG. 8 A, B).

In the case of being exposed to NT, the proinflammatory cytokines IL6 (0.077±0.025 control vs 0.089±0.026 upon LPS stimulation), IL 10 (0.022±0.010 control vs 0.031±0.012 upon LPS stimulation) and IL12p70NT (0.01±0.002 control vs 0.03±0.002 upon LPS stimulation)

were detected in the supernatant after 24 h exposure to LPS (n=3 donors; paired, one-tailed Student-T test, *p<0.05; **p<0.01; FIG. 8A) whilst IL4 (0.016±0.001 control vs 0.018±0.001 upon LPS stimulation), IL6 (0.009±0.009 control vs 0.06±0.06 upon LPS stimulation), IL10 (0.006±0.002 control vs 0.013±0.001 upon LPS stimulation) and IL13 (0.367±0.163 control vs 0.512±0.180 upon LPS stimulation) are the proinflammatory cytokines that were secreted when STR-M were in neuronal medium with CK (n=3 donors; paired, one-tailed Student-T test, *p<0.05; **p<0.01; FIG. 8B). Moreover, cells were positive for the microglia-like markers of Iba1 and Galactin3. These results are indicative that our invention drastically reduced the time for deriving mature functional microglia-like cells, called stroma microglia (STR-M) to only 5 days, clearly distinguishing the method of the present invention from prior art, such as Hinze and Stolzing, 2011.

REFERENCES

Bohlen, C. J. et al. Diverse Requirements for Microglial Survival, Specification, and Function Revealed by Defined-Medium Cultures. *Neuron* 94, 759-773.e758 (2017)

Butovsky, O. et al. Identification of a Unique TGF-β Dependent Molecular and Functional Signature in Microglia. *Nature neuroscience* 17, 131-143 (2014)

Ginhoux, F. et al. Fate mapping analysis reveals that adult microglia derive from primitive macrophages. *Science* 330, 841-845 (2010)

Hickman, S. E. et al. The Microglial Sensome Revealed by Direct RNA Sequencing. *Nature neuroscience* 16, 1896-1905 (2013).

Hinze, A and Stolzing, A. Differentiation of mouse bone marrow derived stem cells toward microglia-like cells, BMC Cell Biology. 2011:12(1):35.

Kierdorf, K. et al. Microglia emerge from erythromyeloid precursors via Pu.1- and Irf8-dependent pathways. *Nature Neuroscience* 16, 273 (2013)

Muffat, J. et al. Efficient derivation of microglia-like cells from human pluripotent stem cells. *Nat Med* 22, 1358-1367, doi:10.1038/nm.4189 (2016).

Nikodemova, M and Watters, J. Efficient isolation of live microglia with preserved phenotypes from adult mouse brain, Journal of Neuroinflammation. 2012: 9(1): 147.

Pandya, H. et al. Differentiation of human and murine induced pluripotent stem cells to microglia-like cells. *Nature neuroscience* 20, 753-759 (2017)

Rahmat Z, Jose S, Ramasamy R, Vidyadaran S. Reciprocal interactions of mouse bone marrow-derived mesenchymal stem cells and BV2 microglia after lipopolysaccharide stimulation, Stem Cell Research & Therapy, 2013:4(1): 12

Schulz, C. et al. A lineage of myeloid cells independent of Myb and hematopoietic stem cells. *Science* 336, 86-90 (2012)

Yang, Y.-H. K., Ogando, C. R., Wang See, C., Chang, T.-Y. & Barabino, G. A. Changes in phenotype and differentiation potential of human mesenchymal stem cells aging in vitro. *Stem Cell Research* & Therapy 9, 131 (2018)

Zhang, Y. et al. An RNA-Sequencing Transcriptome and Splicing Database of Glia, Neurons, and Vascular Cells of the Cerebral Cortex. *The Journal of Neuroscience* 34, 11929-11947 (2014)

The invention claimed is:

1. A method for manufacturing an enriched population of microglia cells, the method comprising the steps of:
   a) providing a sample A and a sample B, both comprising bone marrow stromal cells and/or placenta stromal cells and/or umbilical cord stromal cells;
   b) isolating CD11b$^+$, CD45$^-$ microglia progenitor cells from sample A;
   c) i) contacting sample B with a culturing media comprising serum, thereby expanding the bone marrow stromal cells and/or placenta stroma cells and/or umbilical cord stromal cells into mesenchymal stem cells (MSCs); or
      ii) providing MSCs in a culturing media comprising serum;
   d) contacting the CD11b$^+$, CD45$^-$ microglia progenitor cells of sample A, step (b), with the MSCs of step (c) to generate a sample C;
   e) removing the media comprising serum from sample C;
   f) contacting the serum free sample C of step (e) with a substantially serum free media wherein serum in the substantially serum free media is below detection limits, the substantially serum free media comprising at least one growth factor selected from the group consisting of brain-derived neurotrophic factor (BDNF), nerve growth factor (NGF), neurotrophin-3 (NT-3); neurotrophic 4 (NT-4) and glial cell line-derived neurotrophic factor (GDNF); thereby expanding and differentiating the CD11b+, CD45− microglia progenitor cells;
   g) obtaining an enriched population of microglia cells.

2. The method according to claim 1, wherein the enriched population of microglia cells is in the amount of at least 0.5 million cells.

3. The method according to claim 1, wherein the microglia progenitor cells express genes selected from the group consisting of TMEM119, MERTK1, GPR34, ENTPD1, CX3CR1, Iba1, P2RY12, GPR34, C1QA, PROS1, CD33, GPR56, CABLES1, BHLHE41, TMEM119, TGFBR1, ENTPD1, ITGB2, ITGAM, AIF, IRF8, ADORA3 and PPARD.

4. The method according to claim 1, wherein the substantially serum free media further comprises a cytokine selected from the group consisting of M-CSF, IL34, TGF-beta CX3CL1 and CD200.

5. The method according to claim 1, wherein the microglia progenitor cells express Iba1.

6. An in vitro method for determining the effect of at least one biological agent on a microglia the method comprising:
   i) manufacturing an enriched population of microglia cells by the method of claim 1;
   ii) contacting the enriched population of microglia cells with the biological agent; and
   iii) determining the effect of the biological agent on microglia.

* * * * *